US012611240B2

(12) United States Patent
Thaler et al.

(10) Patent No.: US 12,611,240 B2
(45) Date of Patent: Apr. 28, 2026

(54) INTRAMEDULLARY FIXATION DEVICE

(71) Applicant: CurvaFix, Inc., Bellevue, WA (US)

(72) Inventors: Carly Anderson Thaler, Seattle, WA (US); Steven Charles Dimmer, Bellevue, WA (US)

(73) Assignee: CurvaFix, Inc., Bellevue, WA (US)

( * ) Notice: Subject to any disclaimer, the term of this patent is extended or adjusted under 35 U.S.C. 154(b) by 951 days.

(21) Appl. No.: 17/286,389

(22) PCT Filed: Oct. 17, 2019

(86) PCT No.: PCT/US2019/056799
§ 371 (c)(1),
(2) Date: Apr. 16, 2021

(87) PCT Pub. No.: WO2020/081855
PCT Pub. Date: Apr. 23, 2020

(65) Prior Publication Data
US 2021/0386465 A1      Dec. 16, 2021

Related U.S. Application Data

(60) Provisional application No. 62/906,048, filed on Sep. 25, 2019, provisional application No. 62/747,101, filed on Oct. 17, 2018.

(51) Int. Cl.
*A61B 17/86* (2006.01)

(52) U.S. Cl.
CPC ...... *A61B 17/8685* (2013.01); *A61B 17/8625* (2013.01)

(58) Field of Classification Search
CPC ... A61B 17/86; A61B 17/8685; A61B 17/864; A61B 17/8625
See application file for complete search history.

(56) References Cited

U.S. PATENT DOCUMENTS

| | | | |
|---|---|---|---|
| 2,328,270 A | 8/1943 | Daniel | |
| 2,724,573 A | 11/1955 | Lundquist | |

(Continued)

FOREIGN PATENT DOCUMENTS

| | | | |
|---|---|---|---|
| AT | 509852 A4 | 12/2011 | |
| AT | 509852 B1 | 12/2011 | |

(Continued)

OTHER PUBLICATIONS

US 7,273,482 B2, 09/2007, Dakin et al. (withdrawn)

(Continued)

*Primary Examiner* — Eduardo C Robert
*Assistant Examiner* — Holly Joanna Lane
(74) *Attorney, Agent, or Firm* — Fortem IP LLP

(57) ABSTRACT

An embodiment of a body bead for a bone fracture fixation device, such as a rodscrew, includes at least one pocket and at least one tab. Each of the at least one pocket is configured to engage a respective one of at least one tab of an adjacent body bead and to withstand, without being significantly deformed, a torque of at least three N·m while rotating with the adjacent body bead. And each of the at least one tab is configured to engage a respective one of at least one pocket of another adjacent body bead and to withstand, without being significantly deformed, a torque of at least three N·m while rotating with the other adjacent body bead.

33 Claims, 31 Drawing Sheets

(56) References Cited

U.S. PATENT DOCUMENTS

| | | | |
|---|---|---|---|
| 3,371,725 A | 3/1968 | Wilhelm et al. | |
| 4,098,351 A | 7/1978 | Alessio | |
| 4,489,792 A | 12/1984 | Fahim et al. | |
| 4,491,443 A | 1/1985 | Decaro | |
| 4,605,348 A | 8/1986 | Decaro | |
| 4,706,659 A | 11/1987 | Matthews et al. | |
| 5,108,397 A | 4/1992 | White | |
| 5,167,665 A | 12/1992 | Mckinney | |
| 5,234,435 A | 8/1993 | Seagrave | |
| D346,218 S | 4/1994 | White | |
| 5,300,071 A | 4/1994 | Browner et al. | |
| 5,336,224 A | 8/1994 | Selman | |
| 5,527,309 A | 6/1996 | Shelton | |
| 5,527,310 A | 6/1996 | Cole et al. | |
| 5,593,407 A | 1/1997 | Reis | |
| 5,601,550 A | 2/1997 | Esser | |
| 5,649,925 A | 7/1997 | Barbera | |
| 5,879,352 A | 3/1999 | Filoso et al. | |
| 5,944,719 A | 8/1999 | Leban | |
| 5,993,454 A | 11/1999 | Longo | |
| 6,209,886 B1 | 4/2001 | Estes et al. | |
| 6,340,362 B1 | 1/2002 | Pierer et al. | |
| 6,368,326 B1 | 4/2002 | Dakin et al. | |
| 7,258,692 B2 | 8/2007 | Thelen et al. | |
| 7,410,483 B2 * | 8/2008 | Danitz | A61B 17/072 |
| | | | 606/1 |
| 7,410,489 B2 | 8/2008 | Dakin et al. | |
| 7,625,395 B2 | 12/2009 | Mueckter | |
| 7,632,277 B2 | 12/2009 | Woll et al. | |
| 7,785,325 B1 | 8/2010 | Milbank | |
| 7,846,162 B2 | 12/2010 | Nelson et al. | |
| 8,043,347 B2 | 10/2011 | Jiang et al. | |
| 8,128,626 B2 | 3/2012 | Justin | |
| 8,128,627 B2 | 3/2012 | Justin et al. | |
| 8,157,803 B1 | 4/2012 | Zirkle et al. | |
| 8,206,389 B2 | 6/2012 | Huebner et al. | |
| 8,372,074 B2 | 2/2013 | Milbank | |
| 8,409,257 B2 | 4/2013 | Edidin et al. | |
| 8,439,916 B2 | 5/2013 | Coati et al. | |
| 8,632,543 B2 | 1/2014 | Metzinger et al. | |
| 8,961,516 B2 | 2/2015 | Nelson et al. | |
| 9,060,809 B2 | 6/2015 | Tipirneni et al. | |
| 9,144,506 B2 | 9/2015 | Phelps | |
| 9,155,574 B2 | 10/2015 | Saravia et al. | |
| 9,482,260 B1 | 11/2016 | Krause | |
| 9,498,264 B2 | 11/2016 | Harshman et al. | |
| 9,532,789 B2 | 1/2017 | Coope | |
| 9,615,835 B2 | 4/2017 | Lam et al. | |
| 9,839,435 B2 | 12/2017 | Meek et al. | |
| 10,258,394 B2 | 4/2019 | Harshman et al. | |
| 10,307,188 B2 | 6/2019 | Harshman et al. | |
| 10,973,559 B2 | 4/2021 | Harshman et al. | |
| 11,224,467 B2 * | 1/2022 | Peterson | A61B 17/869 |
| 11,369,421 B2 | 6/2022 | Harshman et al. | |
| 11,419,645 B2 | 8/2022 | Stinson et al. | |
| 11,529,148 B2 * | 12/2022 | Meek | A61B 17/7208 |
| 11,826,262 B2 * | 11/2023 | Glerum | A61B 17/68 |
| 11,832,856 B2 | 12/2023 | Meek et al. | |
| 12,023,074 B2 | 7/2024 | Harshman et al. | |
| 12,167,877 B2 | 12/2024 | Harshman et al. | |
| 2002/0032444 A1 | 3/2002 | Mische | |
| 2002/0077631 A1 | 6/2002 | Lubbers et al. | |
| 2002/0087161 A1 | 7/2002 | Randall et al. | |
| 2002/0198527 A1 | 12/2002 | Muckter | |
| 2003/0078582 A1 | 4/2003 | Heggeness | |
| 2003/0181982 A1 | 9/2003 | Kuslich | |
| 2003/0187449 A1 | 10/2003 | Mccleary et al. | |
| 2003/0229351 A1 | 12/2003 | Tidwell et al. | |
| 2004/0011565 A1 | 1/2004 | Lyon et al. | |
| 2004/0024409 A1 | 2/2004 | Sand et al. | |
| 2004/0050568 A1 | 3/2004 | Orozco | |
| 2004/0102778 A1 | 5/2004 | Huebner et al. | |
| 2004/0215191 A1 | 10/2004 | Kitchen | |
| 2005/0055023 A1 | 3/2005 | Sohngen et al. | |
| 2005/0082824 A1 * | 4/2005 | Luettgen | H01R 35/00 |
| | | | 285/146.1 |
| 2005/0085819 A1 | 4/2005 | Ellis et al. | |
| 2005/0154390 A1 | 7/2005 | Matthis et al. | |
| 2005/0165401 A1 | 7/2005 | Pack | |
| 2006/0074421 A1 | 4/2006 | Bickley et al. | |
| 2006/0264950 A1 | 11/2006 | Nelson et al. | |
| 2007/0083204 A1 | 4/2007 | Sidebotham | |
| 2007/0162132 A1 | 7/2007 | Messerli | |
| 2007/0173834 A1 | 7/2007 | Thakkar | |
| 2007/0208364 A1 | 9/2007 | Smith et al. | |
| 2007/0233111 A1 | 10/2007 | Orbay et al. | |
| 2008/0051786 A1 | 2/2008 | Jensen | |
| 2008/0058722 A1 | 3/2008 | Von et al. | |
| 2008/0077133 A1 | 3/2008 | Schulze | |
| 2008/0077154 A1 | 3/2008 | Edwards et al. | |
| 2008/0108989 A1 | 5/2008 | Parsell et al. | |
| 2008/0161805 A1 | 7/2008 | Saravia et al. | |
| 2008/0181740 A1 | 7/2008 | Waitszies | |
| 2008/0195145 A1 | 8/2008 | Bonutti et al. | |
| 2008/0234676 A1 | 9/2008 | Schulze et al. | |
| 2008/0249628 A1 | 10/2008 | Altarac et al. | |
| 2008/0269745 A1 | 10/2008 | Justin | |
| 2008/0287951 A1 | 11/2008 | Stoneburner et al. | |
| 2008/0294163 A1 | 11/2008 | Chou et al. | |
| 2008/0294164 A1 | 11/2008 | Frank et al. | |
| 2008/0319455 A1 | 12/2008 | Harris et al. | |
| 2009/0024174 A1 | 1/2009 | Stark | |
| 2009/0048672 A1 | 2/2009 | Essenmacher | |
| 2009/0062797 A1 | 3/2009 | Huebner et al. | |
| 2009/0149710 A1 | 6/2009 | Stefanchik et al. | |
| 2009/0192512 A1 | 7/2009 | Sommers | |
| 2009/0216232 A1 | 8/2009 | Buford et al. | |
| 2009/0228008 A1 | 9/2009 | Justin et al. | |
| 2009/0299343 A1 | 12/2009 | Rogers | |
| 2010/0023010 A1 | 1/2010 | Nelson et al. | |
| 2010/0076503 A1 | 3/2010 | Beyar et al. | |
| 2010/0185290 A1 | 7/2010 | Compton et al. | |
| 2010/0217333 A1 | 8/2010 | Mcshane et al. | |
| 2010/0249832 A1 | 9/2010 | Thomas et al. | |
| 2010/0249838 A1 | 9/2010 | Stopek et al. | |
| 2010/0249854 A1 | 9/2010 | Thomas et al. | |
| 2010/0249944 A1 | 9/2010 | Thomas et al. | |
| 2010/0262239 A1 | 10/2010 | Boyden et al. | |
| 2010/0286692 A1 | 11/2010 | Greenhalgh et al. | |
| 2010/0298893 A1 | 11/2010 | Stucki | |
| 2010/0318137 A1 | 12/2010 | Stucki et al. | |
| 2010/0331842 A1 | 12/2010 | Milbank | |
| 2011/0015684 A1 | 1/2011 | Belcheva et al. | |
| 2011/0028974 A1 | 2/2011 | Chemello | |
| 2011/0040282 A1 | 2/2011 | Jihlein | |
| 2011/0046746 A1 | 2/2011 | Rabiner et al. | |
| 2011/0087227 A1 | 4/2011 | Mazur et al. | |
| 2011/0098757 A1 | 4/2011 | Schelling | |
| 2011/0098816 A1 | 4/2011 | Jacob et al. | |
| 2011/0098817 A1 | 4/2011 | Eckhardt et al. | |
| 2011/0119815 A1 | 5/2011 | Paulson et al. | |
| 2011/0144643 A1 | 6/2011 | Lorenz et al. | |
| 2011/0144645 A1 | 6/2011 | Saravia et al. | |
| 2011/0144703 A1 | 6/2011 | Krause et al. | |
| 2011/0153454 A1 | 6/2011 | Dunn et al. | |
| 2011/0184518 A1 | 7/2011 | Trieu | |
| 2011/0184519 A1 | 7/2011 | Trieu | |
| 2011/0184520 A1 | 7/2011 | Trieu | |
| 2011/0196435 A1 | 8/2011 | Forsell | |
| 2011/0218644 A1 | 9/2011 | Meridew et al. | |
| 2011/0230966 A1 | 9/2011 | Trieu | |
| 2011/0238181 A1 | 9/2011 | Trieu | |
| 2011/0264229 A1 | 10/2011 | Donner | |
| 2011/0288598 A1 | 11/2011 | Moed et al. | |
| 2011/0306975 A1 | 12/2011 | Kaikkonen et al. | |
| 2011/0319944 A1 | 12/2011 | Borodic | |
| 2012/0010617 A1 | 1/2012 | Ramos | |
| 2012/0065638 A1 | 3/2012 | Moore | |
| 2012/0078252 A1 | 3/2012 | Huebner et al. | |
| 2012/0078311 A1 | 3/2012 | Huebner et al. | |
| 2012/0083847 A1 | 4/2012 | Huebner et al. | |
| 2012/0083895 A1 | 4/2012 | Conway et al. | |
| 2012/0101533 A1 | 4/2012 | Purcell et al. | |

(56) References Cited

U.S. PATENT DOCUMENTS

| | | | |
|---|---|---|---|
| 2012/0101576 A1 | 4/2012 | Dewey et al. | |
| 2013/0006145 A1 | 1/2013 | Toomey et al. | |
| 2013/0006245 A1 | 1/2013 | Stoneburner et al. | |
| 2013/0012942 A1 | 1/2013 | Nelson et al. | |
| 2013/0131678 A1 | 5/2013 | Dahners | |
| 2013/0144348 A1 | 6/2013 | Schwappach | |
| 2013/0325007 A1 | 12/2013 | Beyar et al. | |
| 2014/0114312 A1 | 4/2014 | Krause | |
| 2014/0296853 A1 | 10/2014 | Wolter | |
| 2014/0309636 A1 | 10/2014 | Meek et al. | |
| 2014/0358146 A1 | 12/2014 | Meek et al. | |
| 2015/0012051 A1* | 1/2015 | Warren | A61B 17/8685 606/310 |
| 2015/0038970 A1 | 2/2015 | Coope | |
| 2015/0157370 A1 | 6/2015 | Gross | |
| 2015/0257800 A1* | 9/2015 | Harshman | A61B 17/8897 606/62 |
| 2015/0297245 A1 | 10/2015 | Lam et al. | |
| 2017/0014170 A1 | 1/2017 | Fallin et al. | |
| 2017/0020585 A1 | 1/2017 | Harshman et al. | |
| 2017/0049460 A1 | 2/2017 | Coope | |
| 2017/0164953 A1 | 6/2017 | Lam et al. | |
| 2017/0238977 A1* | 8/2017 | Harshman | A61B 17/7283 |
| 2018/0092681 A1 | 4/2018 | Lutz | |
| 2018/0296227 A1 | 10/2018 | Meek et al. | |
| 2019/0120282 A1 | 4/2019 | Krause | |
| 2019/0231401 A1 | 8/2019 | Harshman et al. | |
| 2019/0282280 A1 | 9/2019 | Harshman et al. | |
| 2020/0038646 A1 | 2/2020 | Sweeney et al. | |
| 2020/0054372 A1 | 2/2020 | Stinson et al. | |
| 2020/0138492 A1 | 5/2020 | Kavanagh | |
| 2021/0220027 A1 | 7/2021 | Harshman et al. | |
| 2021/0322070 A1 | 10/2021 | Koch et al. | |
| 2021/0353338 A1 | 11/2021 | Meek et al. | |
| 2022/0287744 A1 | 9/2022 | Harshman et al. | |
| 2022/0354549 A1 | 11/2022 | Stinson et al. | |
| 2023/0157708 A1 | 5/2023 | Meek et al. | |
| 2023/0248392 A1* | 8/2023 | Whittaker | A61B 17/7233 606/86 R |
| 2023/0404636 A1* | 12/2023 | Whittaker | A61B 17/8685 |
| 2024/0081880 A1 | 3/2024 | Meek et al. | |
| 2024/0307098 A1 | 9/2024 | Harshman et al. | |
| 2025/0064489 A1 | 2/2025 | Harshman et al. | |

FOREIGN PATENT DOCUMENTS

| | | | |
|---|---|---|---|
| CA | 2725324 A1 | 11/2009 | |
| CN | 2662839 Y | 12/2004 | |
| CN | 2699846 Y | 5/2005 | |
| CN | 101208053 A | 6/2008 | |
| CN | 101633119 A | 1/2010 | |
| CN | 101636119 A | 1/2010 | |
| CN | 102793579 A | 11/2012 | |
| CN | 103025257 A | 4/2013 | |
| CN | 103200887 A | 7/2013 | |
| CN | 103813764 A | 5/2014 | |
| CN | 104203132 A | 12/2014 | |
| CN | 104837425 A | 8/2015 | |
| CN | 104203132 B | 8/2017 | |
| CN | 107106217 A | 8/2017 | |
| CN | 112955087 A | 6/2021 | |
| EP | 0078619 A2 | 5/1983 | |
| EP | 1941838 A1 | 7/2008 | |
| EP | 2779928 A1 | 9/2014 | |
| EP | 3326558 A1 | 5/2018 | |
| EP | 3522803 A1 | 8/2019 | |
| EP | 3866712 A1 | 8/2021 | |
| GB | 1494553 A | 12/1977 | |
| NO | 2009143374 A2 | 11/2009 | |
| WO | 2007009123 A2 | 1/2007 | |
| WO | 2008116175 A2 | 9/2008 | |
| WO | 2008120877 A1 | 10/2008 | |
| WO | 2010124230 A1 | 10/2010 | |
| WO | 2011067668 A1 | 6/2011 | |
| WO | 2011119815 A2 | 9/2011 | |
| WO | 2011153454 A2 | 12/2011 | |
| WO | 2012107913 A2 | 8/2012 | |
| WO | 2013063145 A1 | 5/2013 | |
| WO | 2013071432 A1 | 5/2013 | |
| WO | 2014075165 A1 | 5/2014 | |
| WO | 2014075184 A1 | 5/2014 | |
| WO | 2015134750 A1 | 9/2015 | |
| WO | 2016061173 A1 | 4/2016 | |
| WO | 2018067888 A1 | 4/2018 | |
| WO | 2020077457 A1 | 4/2020 | |
| WO | 2020081855 A1 | 4/2020 | |

OTHER PUBLICATIONS

International Searching Authority, "International Search Report and Written Opinion from PCT Application No. PCT/US2019/056799", from Foreign Counterpart to U.S. Appl. No. 17/286,389, filed Mar. 24, 2020, pp. 1 through 18, Published: WO.

International Searching Authority, "Invitation to Pay Additional Fees from PCT Application No. PCT/US2019/056799", from Foreign Counterpart to U.S. Appl. No. 17/286,389, filed Jan. 28, 2020, pp. 1 through 10, Published: WO.

International Bureau, "International Preliminary Report on Patentability from PCT Application No. PCT/US2019/056799", from Foreign Counterpart to U.S. Appl. No. 17/286,389, filed Apr. 29, 2021, pp. 1 through 11.

International Search Report and Written Opinion mailed Dec. 11, 2017, International Application No. PCT/US2017/055442, 9 pages.

International Search Report and Written Opinion mailed Feb. 5, 2020, International Application No. PCT/CA2019/051471, 13 pages.

International Search Report and Written Opinion mailed Feb. 9, 2016, International Application No. PCT/US2015/055441, 8 pages.

International Search Report and Written Opinion mailed Feb. 20, 2014, International Application No. PCT/CA2013/050870, 11 pages.

International Search Report and Written Opinion mailed Feb. 26, 2013, International Application No. PCT/CA2012/050808, 10 pages.

International Search Report and Written Opinion mailed Jul. 31, 2013, International Application No. PCT/CA2012/050807, 8 pages.

International Search Report and Written Opinion mailed May 27, 2015, International Application No. PCT/US2015/018969, 5 pages.

"UT Southwest Medical Surgeons Market Pelvic Fracture Device", Accessed at http://www.texasbusiness.com/ut-southwest-medical-surgeons-market-pelvic-fracture-device-cms-4418, Texas Business. com, Apr. 22, 2011, pp. 1-5.

Barry et al., "Flexible intramedullary nails for fractures in children", Aspects of Current Management, vol. 86-B, No. 7, British Editorial Society of Bone and Joint Surgery, Sep. 2004, pp. 1-7.

Cheung et al., "A New Halo-Pelvic Apparatus", Spine, vol. 28, No. 3, pp. 305-308.

Ganz et al., "Surgical dislocation of the adult hip", The Journal of Bone and Joint Surgery (Br), vol. 83-B, No. 8, British Editorial Society of Bone and Joint Surgery, Nov. 2004, pp. 1119-1124.

Griffin et al., "Vertically Unstable Pelvic Fractures Fixed with Percutaneous Iliosacral Screws: Does Posterior Injury Jattem Prediction Fixation Failure?", Journal of Orthopedic Trauma, vol. 17, No. 6, Lippincott Williams, and Wilkins, Inc., Jan. 2006, pp. 399-405.

Miller et al., "Variations in Sacral Morphology and Implications for Iliosacral Screw Fixation", Journal of the American Academy of Orthopaedic Surgeons, vol. 20, No. 1, American Academy of Orthopaedic Surgeons, Jan. 2012, pp. 8-16.

Novick, "Pelvic Fractures/Acetabular Fractures", Hospital for Special Surgery, Mar. 30, 2006, HSS.edu, Mar. 30, 2006, pp. 1-9.

Novick, "Pelvic Fractures/Acetabular Fractures—An Interview with Dr. David L. Helfet", Hospital for Special Surgery, accessed at http://www.hss.edu/conditions—pelvic-acetabulum-fractures.asp, Mar. 30, 2006, 10 Pages.

Starr, "Fractures of the Pelvic Ring", Rockwood & Green's Fractures in Adults 6th Edition, Chapter 41, accessed on Feb. 4, 2014, Lippincott Williams & Wilkins, pp. 1-40.

(56)  References Cited

OTHER PUBLICATIONS

Starr et al., "Superior Pubic Ramus Fractures Fixed With Percutaneous Screws: What Predicts Fixation Failure?", Journal of Orthopaedic Trauma, vol. 22, No. 2, Lippincott Williams and Wilkins, Feb. 2008, pp. 81-87.

Vaidya, R. et al., "Complications of Anterior Subcutaneous Internal Fixation for Unstable Pelvis Fractures: A Multicenter Study", Clinical Orthopaedics and Related Research, vol. 470, No. 8, Springer, Aug. 2012, pp. 1-8.

* cited by examiner

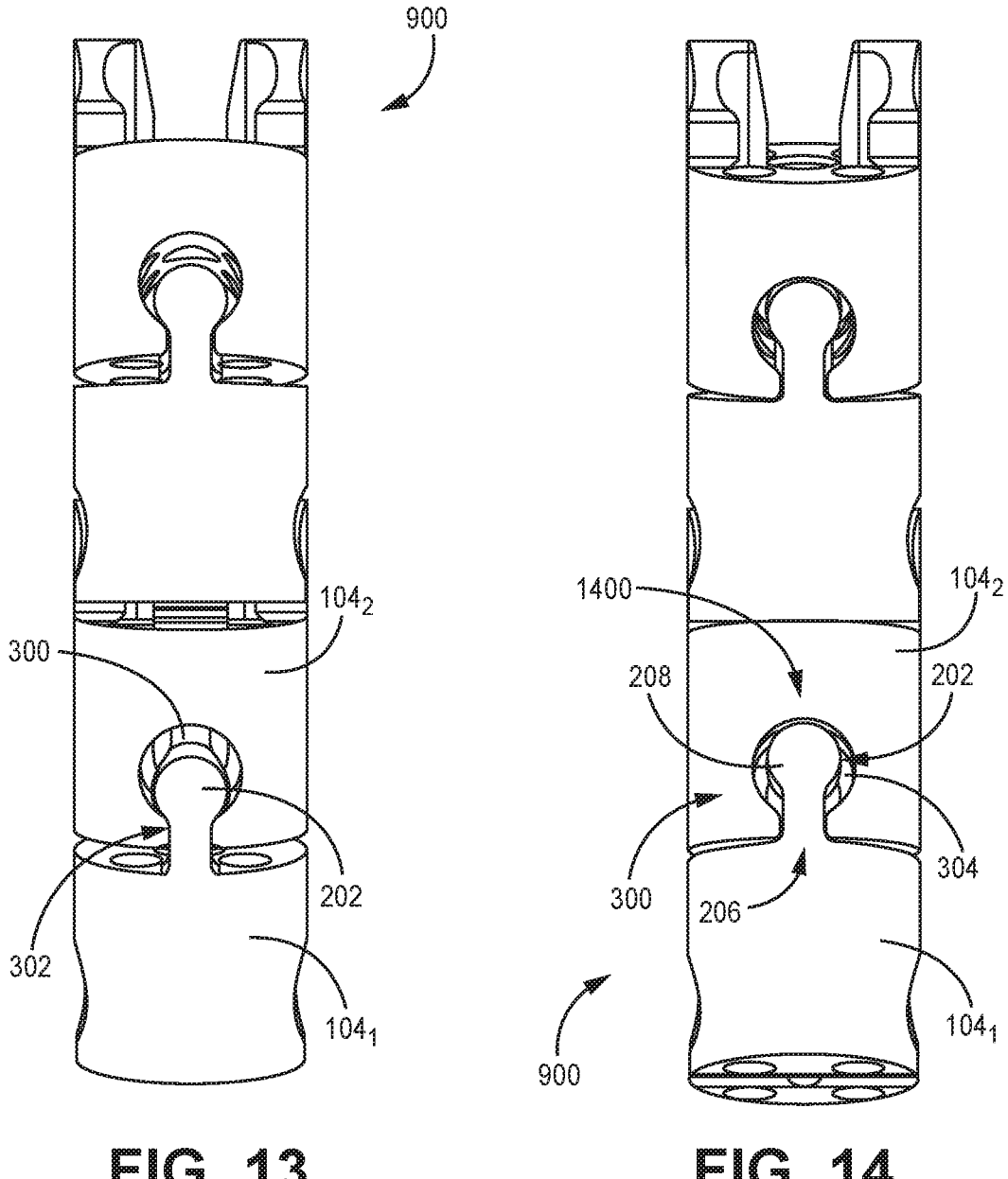
FIG. 13          FIG. 14

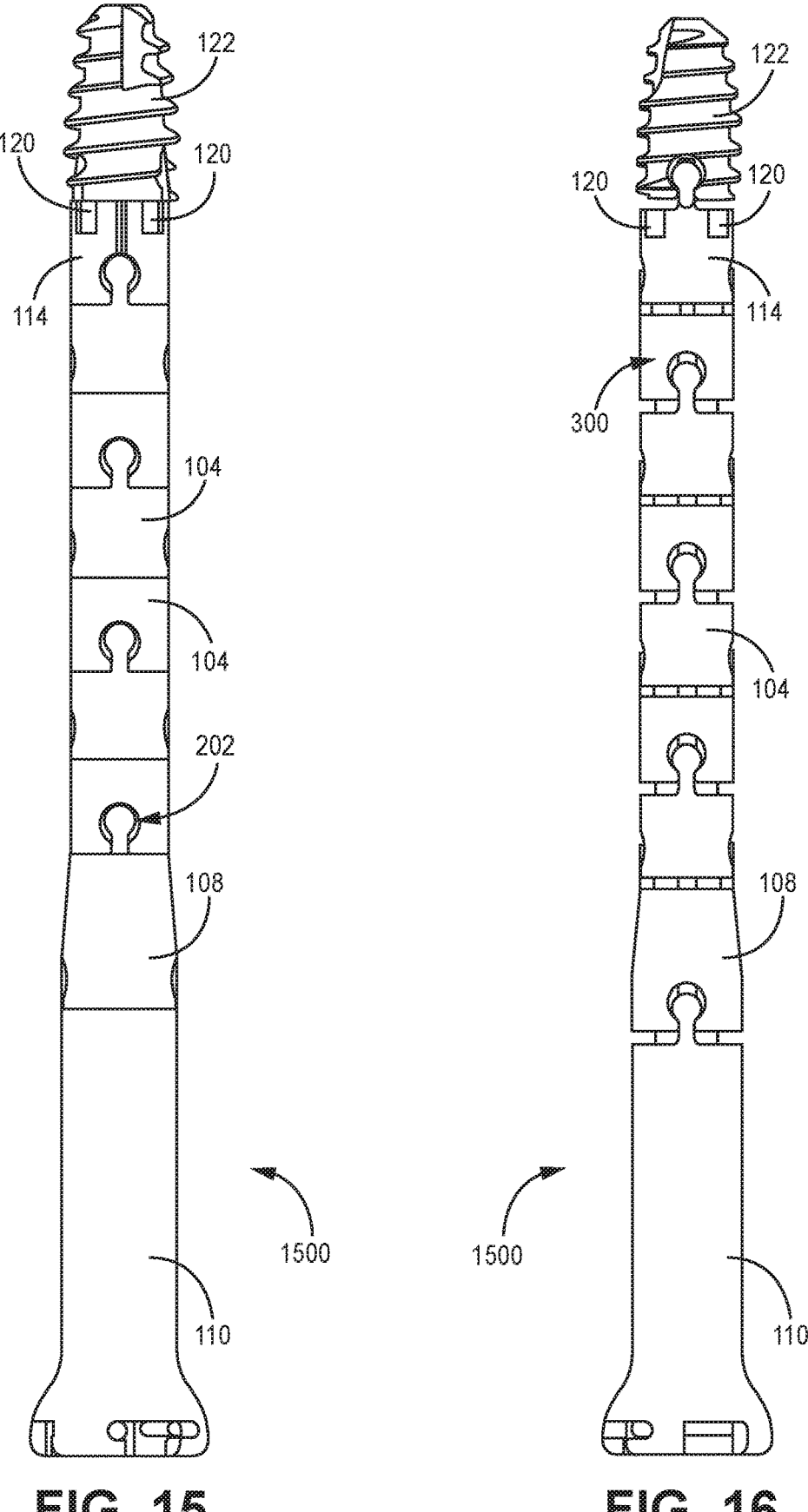
FIG. 15                    FIG. 16

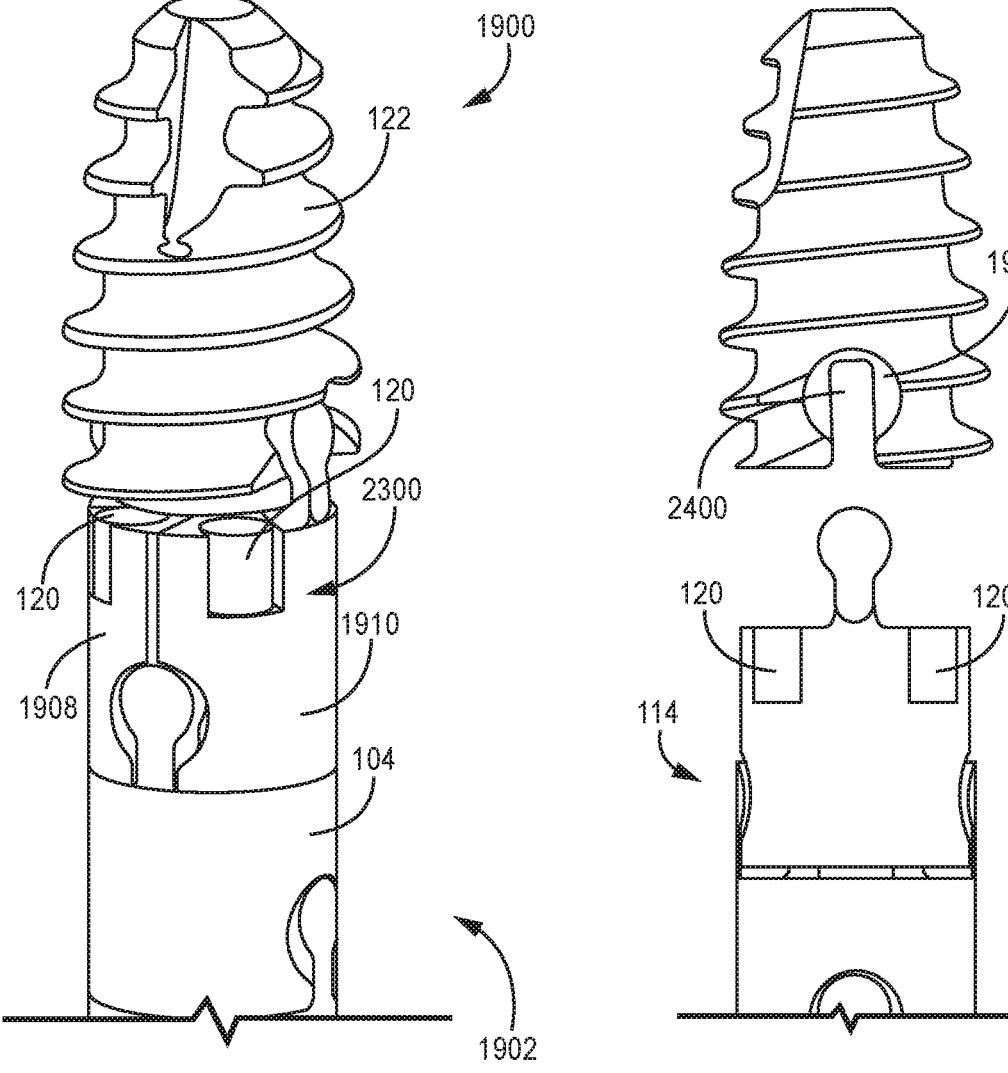
FIG. 23          FIG. 24

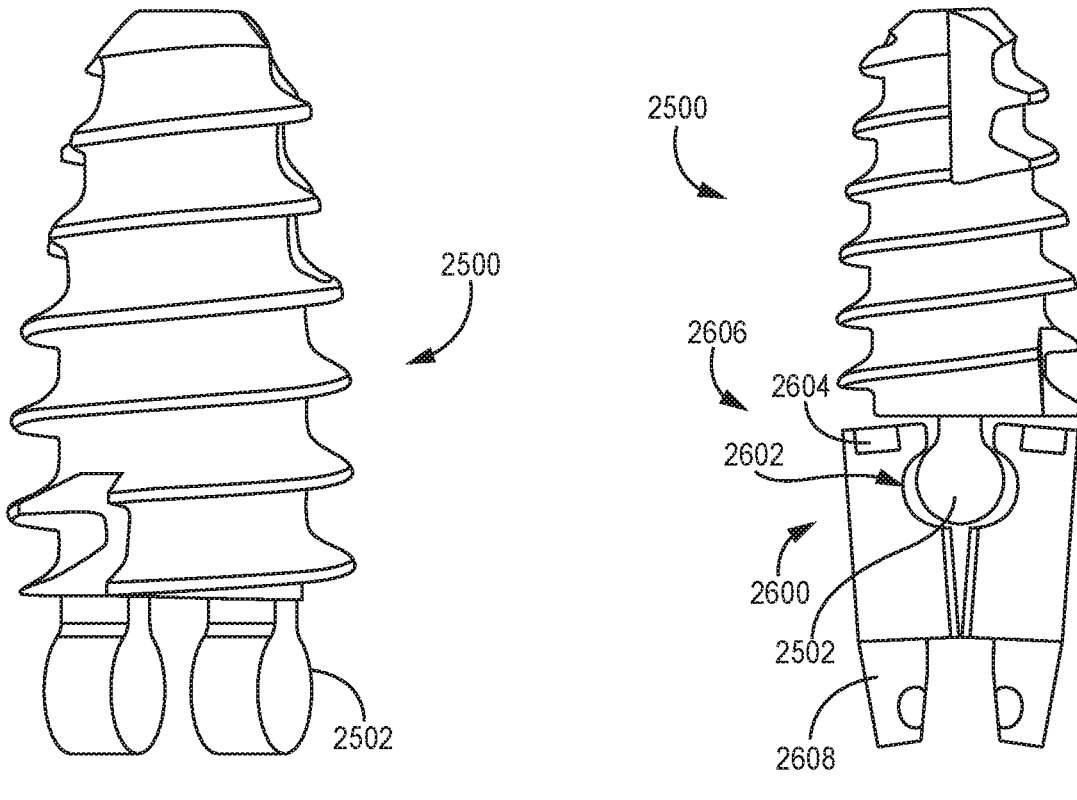
FIG. 25                FIG. 26

INTRAMEDULLARY FIXATION DEVICE

RELATED AND PRIORITY APPLICATIONS

This patent application claims priority to: U.S. Provisional Patent Application Ser. No. 62/747,101, which is titled INTRAMEDULLARY FIXATION DEVICE, and which was filed 17 Oct. 2018; and U.S. Provisional Patent Application Ser. No. 62/906,048, which is titled INTRAMEDULLARY FIXATION DEVICE, and which was filed 25 Sep. 2019. The aforementioned provisional patent applications are incorporated herein by reference.

This application claims priority to International Patent Application No. PCT/US2019/056799 filed on Oct. 17, 2019.

SUMMARY

The following publications describe rodscrews for fixating one or more pelvic fractures, and are incorporated herein by reference: U.S. Pat. No. 9,839,435; US 2017/0020585; US 2017/0238977; PCT/US2017/055442; WO 2018/067888; WO 2013/071432; U.S. Pat. No. 9,498,264; US 2017/0238977; U.S. Provisional Patent Application Ser. No. 62/747,039, which is titled USE OF RODSCREW IN MEDICAL APPLICATIONS OTHER THAN TREATING A FRACTURE OF THE PELVIS, and which was filed 17 Oct. 2018; and U.S. Provisional Patent Application Ser. No. 62/905,925, which is titled BONE-FIXATION DEVICE AND SYSTEM, and which was filed 25 Sep. 2019.

An intramedullary device, also called a rodscrew, for fixating one or more fractures of one or more bones, such as one or more pelvic bones, is described, according to one or more embodiments.

In an embodiment, during an implant procedure, the rodscrew is first in a flexible configuration (also called "mode" or "state") in which the rodscrew can flex and bend as a surgeon is implanting the rodscrew through a hole in a fractured bone and through a curved pathway within an intramedullary space of the bone so that the rodscrew spans the one or more fractures of the bone.

After the rodscrew is implanted, and, therefore, after the rodscrew has acquired the shape of the intramedullary pathway, which is often curved in at least two dimensions, the surgeon transitions the rodscrew from its flexible configuration to a rigid, stiff configuration in which the rodscrew fixates the bone by holding together, in proper alignment along the fracture line(s), the two or more sections of the fractured bone. In the rigid configuration, the rodscrew also can support loads that the rodscrew may experience during the fracture-healing process.

An embodiment of a rodscrew, such as for use in the treatments and procedures described above and below, includes at least two internal cables, but often includes three, four, or more cables for added stability, and the ability to lock into any curved shape that the rodscrew can attain while in its flexible configuration.

An embodiment of a body bead for a bone-fracture fixation device, such as a rodscrew, includes at least one pocket and at least one tab. Each of the at least one pocket is configured to engage a respective one of at least one tab of an adjacent body bead and to withstand, without being significantly deformed, a torque of at least three N·m while rotating with the adjacent body bead. And each of the at least one tab is configured to engage a respective one of at least one pocket of another adjacent body bead and to withstand, without being significantly deformed, a torque of at least three N·m while rotating with the other adjacent body bead.

An embodiment of a bone-fracture fixation device, such as a rodscrew, includes first and second interfaces, a body, three or more cables, and a locking interface. The first interface is configured to engage a bone, and the second interface also is configured to engage a bone. The body includes a series of beads disposed between, and coupled to, the first interface and the second interface, each bead in the series of beads including three or more cable through holes and each bead configured to withstand, without being significantly deformed, a torque of at least three N·m. Each of the three or more cables is disposed in a respective one of the cable through holes, and the locking interface is disposed adjacent to one of the first and second interfaces, is configurable to hold the cables to cause the body to be rigid in a curved configuration, and is configurable to release the cables to cause the body to be flexible.

Another embodiment of a body bead for a bone-fracture fixation device, such as a rodscrew, includes a base, at least one tab, and at least one pocket. The base has first and second ends and a base width. Each of the at least one tab protrudes from the first end, is configured to engage a respective one of at least one pocket of an adjacent body bead, and has a respective tab thickness at least approximately one fourth the base width. And each of the at least one pocket is formed in the base at the second end and is configured to engage a respective one of at least one tab of another adjacent body bead.

Yet another embodiment of a bone-fracture fixation device, such as a rodscrew, includes a distal interface, a proximal interface, a body, and a locking interface. The distal interface is configured to engage a bone, and the body includes a series of beads disposed between, and coupled to, the distal and proximal interfaces, each bead in the series of beads including a base having first and second ends and a base width, at least one tab each protruding from the first end, configured to engage a respective one of at least one pocket of an adjacent body bead and having a respective tab thickness at least approximately one fourth the base width, and at least one pocket each formed in the base at the second end and configured to engage a respective one of at least one tab of another adjacent body bead. And the locking interface is disposed adjacent to the proximal interface, is configurable to cause the body to be rigid in a curved configuration, and is configurable to cause the body to be flexible.

Each value, quantity, or attribute herein preceded by "substantially," "approximately," "about," a form or derivative thereof, or a similar term, encompasses a range that includes the value, quantity, or attribute ±20% of the value, quantity, or attribute, or a range that includes ±20% of a maximum difference from the value, quantity, or attribute, or ±20% of the difference between the range endpoints. For example, an "approximate" range of b-c is a range of b−20%·(c−b) to c+20%·(c−b). Furthermore, the terms "a," "an," and "the" can indicate one or more than one of the objects that they modify.

BRIEF DESCRIPTION OF THE DRAWINGS

FIG. 13 is a plan view of the portion of the rodscrew of FIGS. 9-12 curved in a plane orthogonal to the plane of FIG. 13 in a direction "into" the page of FIG. 13, according to an embodiment.

FIG. 14 is a plan view of the portion of the rodscrew of FIGS. 9-13 curved in a plane orthogonal to the plane of FIG. 14 in a direction "out from" the page of FIG. 14, according to an embodiment.

FIG. 15 is a plan view of a rodscrew having a body similar to the body described in conjunction with FIGS. 9-14, with the beads of the body compressed together, according to an embodiment.

FIG. 16 is a plan view of a rodscrew having a body similar to the body described in conjunction with FIGS. 9-14, with the beads of the body spread apart, according to an embodiment.

FIGS. 20-23 are respective views of a distal-end portion of a rodscrew including a two-piece anchor bead and a distal end, according to an embodiment.

FIG. 24 is an exploded view of the rodscrew distal end and anchor bead of FIGS. 19-23, according to an embodiment.

FIG. 25 is an isometric view of a rodscrew distal end having tabs instead of pockets, according to an embodiment.

FIG. 26 is a side view of the rodscrew distal end of FIG. 25 and a two-piece anchor bead, according to an embodiment.

DETAILED DESCRIPTION

Each value, quantity, or attribute herein preceded by "substantially," "approximately," "about," a form or derivative thereof, or a similar term, encompasses a range that includes the value, quantity, or attribute ±20% of the value, quantity, or attribute, or a range that includes ±20% of a maximum difference from the value, quantity, or attribute, or ±20% of the difference between the range endpoints. For example, an "approximate" range of b-c is a range of b–20%·(c–b) to c+20%·(c–b). Furthermore, the terms "a," "an," and "the" can indicate one or more than one of the objects that they modify.

Figure 1:
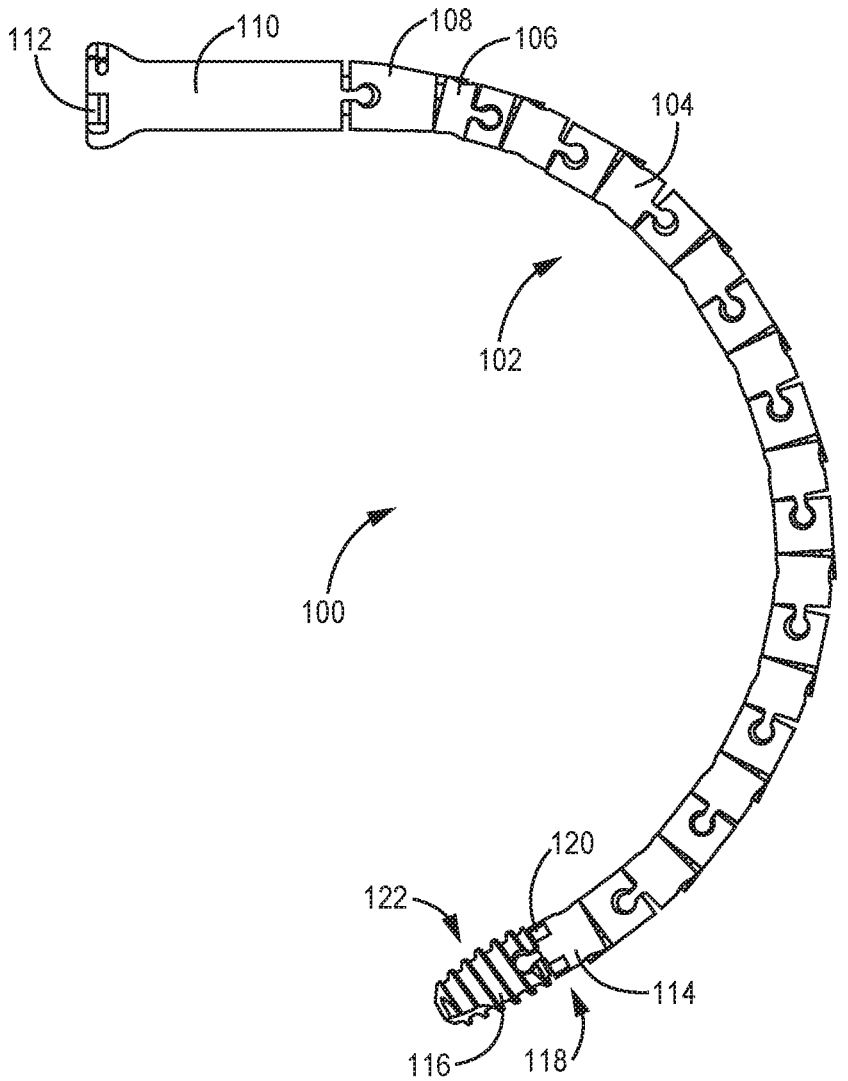
FIG. 1 is a plan view of a rodscrew in a curved configuration, according to an embodiment.

FIG. 1 is a plan view of a rodscrew 100 in a curved configuration, according to an embodiment.

Figure 2:
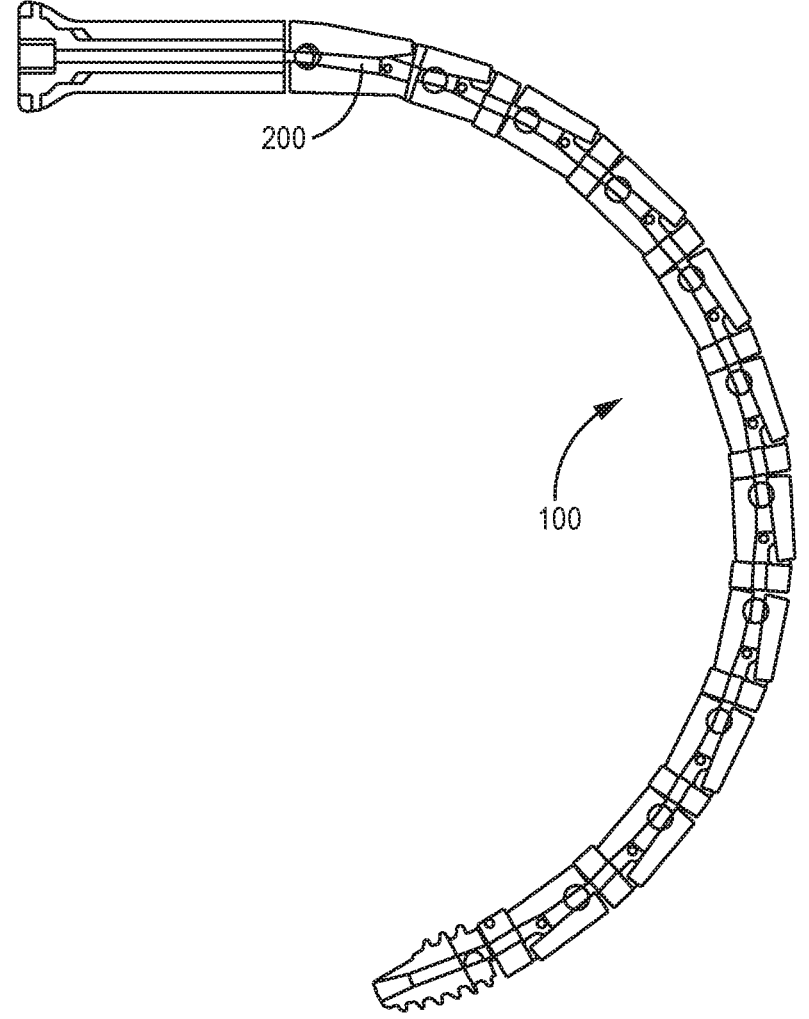
FIG. 2 is a cross-sectional view of the rodscrew of FIG. 1, according to an embodiment.

FIG. 2 a cross-sectional view of the rodscrew 100 of FIG. 1, according to an embodiment.

Referring to FIGS. 1-2, an intramedullary device 100, hereinafter called a "rodscrew," is configurable in a curved shape, according to an embodiment; although shown as being shaped in a single curve in a single plane, the rodscrew may be configured to include multiple curves, where one of the curves is in a different plane than at least another one of the curves. The rodscrew 100 includes a body 102 formed from one or more main-body beads 104, one or more spacer beads 106, one or more transition beads 108, a proximal housing (hereinafter "proximal end") 110, a proximal lock 112, one or more anchor beads 114, a distal bead (hereinafter "distal end") 116, and flexible members, here cables, 118 having ends 120. One can use different combinations and numbers of main-body and spacer beads 104 and 106 to create different-length devices from, e.g., 110 millimeters (mm) to 210 mm long. Longer or shorter devices can also be be created for bone fixation in longer or shorter intramedullary bone pathways. One or more spacer beads 106 can be placed anywhere along the body 102 of the rodscrew 100 between the transition bead(s) 108 and the anchor bead(s) 114. For example, each main-body bead 104 is approximately 7.5 mm long (not including tabs) and each spacer bead 106 comes in versions that are, respectively, approximately 5.0, 10.0, and 12.5 mm long (not including tabs); in an embodiment, the rodscrew 100 is available in lengths that are even increments of 10 mm (e.g., 20 mm, 40 mm, 60 mm).

The main-body beads 104 are further described below in conjunction with FIGS. 3-8.

Other than its length, each spacer bead 106 is similar to a main-body bead 104.

Each transition bead 108 is configured to couple the proximal end 110 to the body 102.

The proximal end 110 includes a proximal lock 112, which is a mechanism configured to cause the remaining portion (e.g., the body 104 and the distal end 116) of the rodscrew 100 to be flexible while the proximal lock is in an unlocked state, and which is configured to cause the remaining portion of the rodscrew to be rigid while the proximal lock is in a locked state.

Each anchor bead 114 (only one anchor bead shown in FIG. 1) is configured to couple the distal end 116 to the body 102, and the anchor bead closest to the distal end includes cable receptacles, also called cable bores, configured to receive the cable ends 120.

The distal end 116 is configured to hold the rodscrew 100 in a stable position and orientation while the rodscrew is implanted in an intramedullary space of the bone (not shown in FIGS. 1-2); for example, the distal end includes relatively sharp threads 122 configured to engage bone by being screwable into the bone.

The cables 118, also called flexible members, extend from the last anchor bead 114 to, and into, the proximal end 110. The flexible members can also be metal wires, fibers, plastic or other fibers (e.g. carbon fiber) in construction. While the proximal lock 112 is in an unlocked state, the cables 118 are free to slide relative to one another in an axial dimension (length dimension of the rodscrew) and to acquire a respective bend radius while the rodscrew 100 is in its flexible state and is curved. But while the proximal lock 112 is in a locked state, the lock prevents the cables 118 from sliding relative to one another in an axial dimension, and the cables are configured to maintain, rigidly, the rodscrew 100 in a shape (e.g., a curved shape) that the rodscrew acquired while it was in its flexible configuration. In an embodiment, the rodscrew 100 includes four cables 118, although the rodscrew can include fewer than, or more than, four cables. Furthermore, each cable 118 can be formed from any suitable material, such as steel or another metal, and can include multiple filaments that are wound about one another, or that are otherwise configured, to form the cable.

The end caps 120 are attached to the ends of the cables 118, e.g., by press fitting, and keep the distal ends of the cables from "slipping through" the most-distal anchor bead 114. The end caps may be made from any suitable material, such as steel or another metal.

Furthermore, although not shown in FIG. 1, the proximal ends of the cables 118, which ends are, in FIG. 1, hidden from view by a housing of the proximal end 110, may also be fitted with end caps that are the same as, or that are similar to, the end caps 120.

Still referring to FIG. 1 and as described below in conjunction with FIGS. 3-8, the body beads 104, spacer beads 106 (if present), transition bead(s) 108, proximal end 110, anchor bead(s) 114, and distal end 116 are constructed to withstand the torques and other forces that the rodscrew 100 may experience during a rodscrew-implant procedure, during healing of the fixated fracture(s), and during a rodscrew-removal procedure (also called a rodscrew-extraction procedure). A study was performed in which rodscrews similar to the rodscrews 100 were implanted in pelvic bones of multiple live sheep, and remained implanted in the sheep for over 60 days, during which time bone overgrew portions (e.g., the device body 102) of the rodscrews during the healing process. The average torque required to remove the rodscrews from the bone by, e.g., unscrewing the distal ends 116 from the respective bones after bone healing, was 2.96 Newton meters (N·m). Consequently, in an embodiment, each of the aforementioned components of the rodscrew 100 is constructed to withstand a torque having a magnitude of 2 N·m or higher, for example, within a range of approximately 2 N·m–9 N·m, or with a minimum of at least 3 N·m before deformation of any of the device mechanical interfaces occurs.

Referring to FIG. 2, the rodscrew 100 also includes a guidewire bore 200 (also called a guidewire or central opening or through hole) along a longitudinal axis of the rodscrew, according to an embodiment. The bore 200 is configured to receive a guidewire (not shown in FIG. 2) such that during an implantation procedure, a surgeon can slide the rodscrew 100 over a guidewire that was previously inserted into an intramedullary space of a fractured bone (surgeon, guidewire, intramedullary space, and bone not shown in FIG. 2). The surgeon using a guidewire in such a manner can facilitate the implantation of the rodscrew 100. Typically, after the rodscrew 100 is implanted, the surgeon removes the guidewire through the central opening 200.

Furthermore, due to the orientation of the cross section of the rodscrew 100, the cables 118 (FIG. 1) are not visible in FIG. 2.

Referring to FIGS. 1-2, alternate embodiments of the rodscrew 100 are contemplated. For example, although the rodscrew 100 is described as including one spacer bead 106, the rodscrew may include no spacer beads, or multiple spacer beads. Furthermore, although the rodscrew 100 is described as including one transition bead 108 and one anchor bead 114, the rodscrew may include no spacer transition beads, no anchor beads, multiple transition beads, or multiple anchor beads. Moreover, embodiments described in conjunction with FIGS. 3-39 may be applicable to the rodscrew 100 of FIGS. 1-2.

Figure 3:
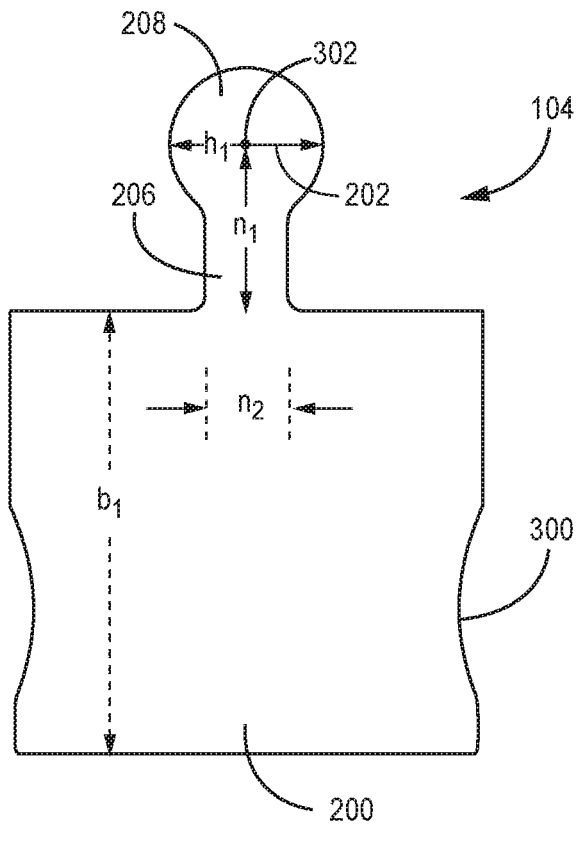
FIG. 3 is a side view of a body segment, or body bead, of a body of the rodscrew of FIGS. 1 and 2, according to an embodiment.

FIG. 3 is a side view of a body bead 104 of the rodscrew 100 of FIGS. 1 and 2, according to an embodiment.

Figure 4:
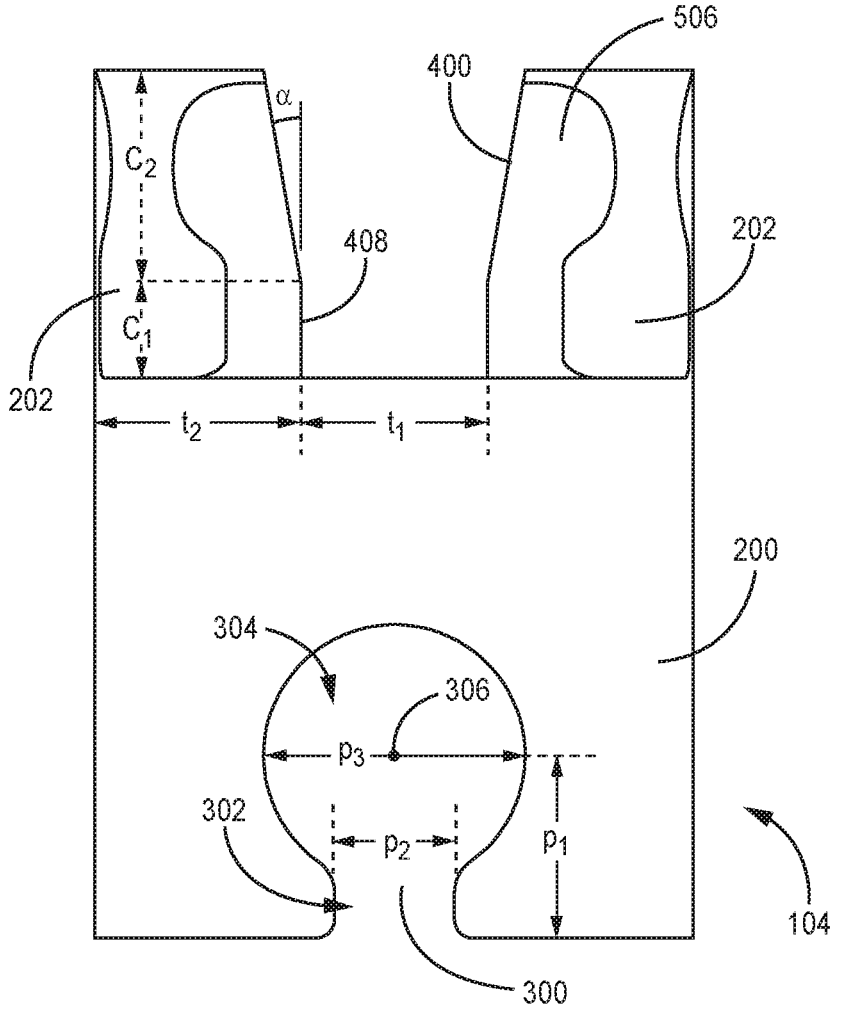
FIG. 4 is a side view of the body bead of FIG. 3 rotated about its vertical axis by 90° relative to the bead of FIG. 3, according to an embodiment.

FIG. 4 is a side view of the body bead 104 of FIG. 3 rotated about its vertical axis by 90° relative to the body bead of FIG. 3, according to an embodiment.

Figure 5:
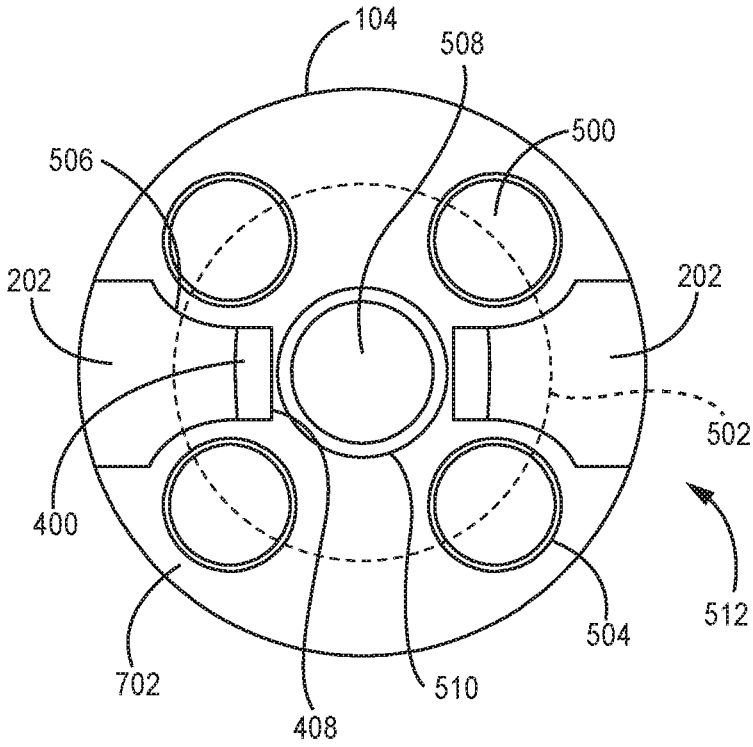
FIG. 5 is a top view of the body bead of FIGS. 3-4, according to an embodiment.

FIG. 5 is a top view of the body bead 104 of FIGS. 3-4, according to an embodiment.

Figure 6:
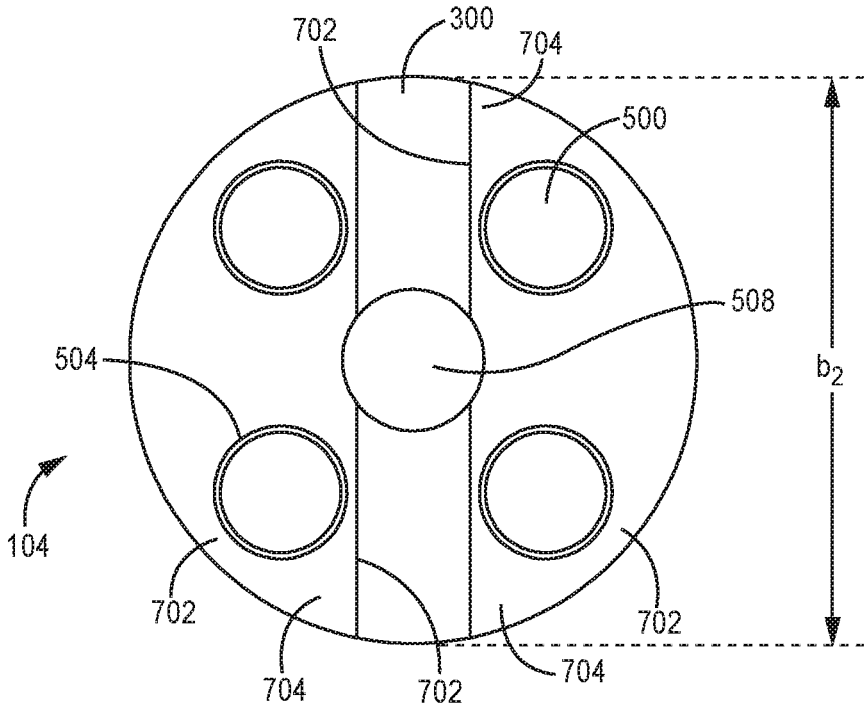
FIG. 6 is a bottom view of the body bead of FIGS. 3-5, according to an embodiment.

FIG. 6 is a bottom view of the body bead 104 of FIGS. 3-5, according to an embodiment.

Figure 7:
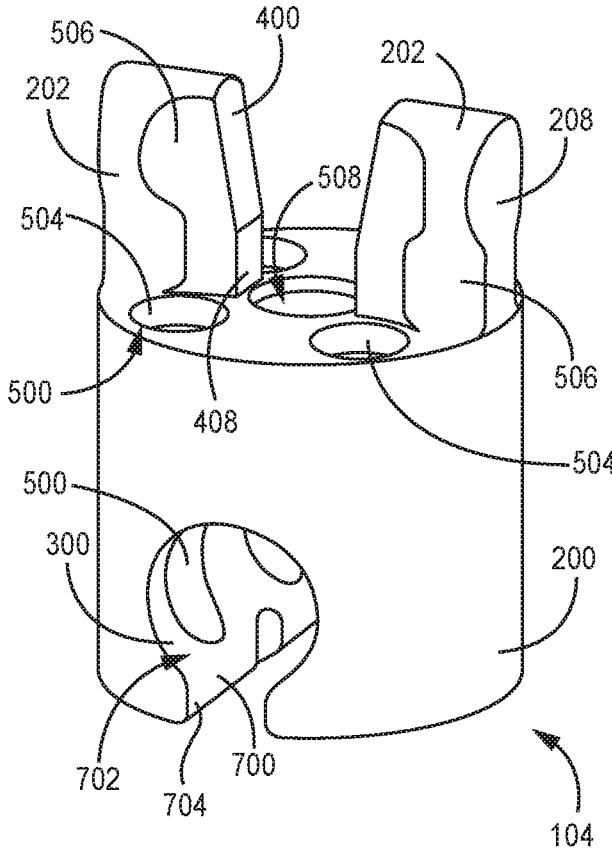
FIG. 7 is an isometric view of the body bead of FIGS. 3-6 in a vertical orientation, according to an embodiment.

FIG. 7 is an isometric view of the body bead 104 of FIGS. 3-6 in a vertical orientation, according to an embodiment.

Figure 8:
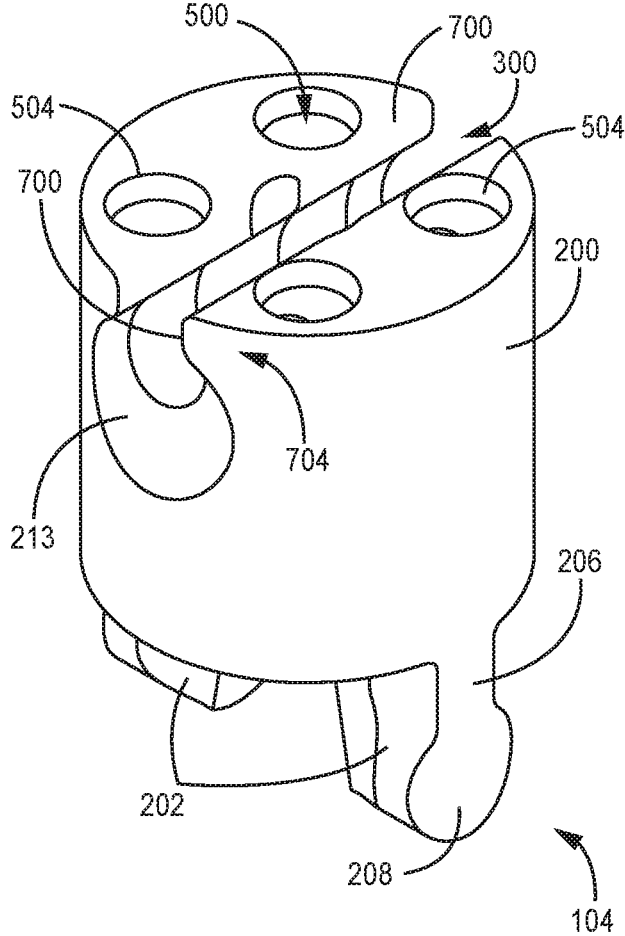
FIG. 8 is an isometric view of the body bead of FIGS. 3-7 in a vertical orientation that is opposite to the vertical orientation of FIG. 7, according to an embodiment.

And FIG. 8 is an isometric view of the body bead 104 of FIGS. 3-7 in a vertical orientation that is opposite to the vertical orientation of the body bead in FIG. 7, according to an embodiment.

Referring to FIGS. 3-8, the body bead 104 includes a base 200, two tabs 202, one pocket 300, four cable bores, or through holes, 500, and a central bore, or through hole, 508, according to an embodiment. The body bead 104 can be made from any suitable material, such as surgical steel, titanium, another metal, or a polymer such as PEEK. The cable through holes 500 are evenly spaced (e.g., approximately 90° apart) around a periphery of the base 200, and the center through hole 508 is centered within the base.

The base 200 has a height $b_1$ and a diameter $b_2$. For example, the height $b_1$ may be in a range of approximately, 6.5 mm-8.5 mm, and may be, for example, approximately 7.5 mm, and the diameter $b_2$ may be in a range of approximately 6.5 mm-24.0 mm, and may be, for example, approximately 8.0 mm.

Each of the tabs 202 has a "lollipop" shape, with a stem, or neck, 206 and a head 208. The tabs 202 are separated by a distance $t_1$, which in an embodiment, is in a range of approximately 1.5 mm-3.5 mm, and may be, for example, approximately 2.5 mm. The neck 206 has a height, $n_1$, from the base 200 to a center 302 of the head 208, and has a width $n_2$. In an embodiment, $n_1$ is in a range of approximately 1.8 mm-3.8 mm, and may be, for example, 2.8 mm, and $n_2$ is in in a range of approximately 0.4-2.4 mm, and may be, for example, 1.4 mm. And the head 208 has a diameter $h_1$, which, in an embodiment, is in a range of approximately 1.6 mm-3.6 mm, and may be, for example, 2.6 mm. Furthermore, each of the tabs 202 has a respective chamfered surface 400 that begins at a height $c_1$ above the top surface of the base 200, extends for a perpendicular height $c_2$, and makes an angle $\alpha$ with respect to the height dimension of the tab. In an embodiment, $c_1$ is in a range of approximately 0.3 mm-2.3 mm, and may be, for example, 1.3 mm; $c_2$ is in a range of approximately 1.8 mm-3.8 mm, and may be, for example, 2.8 mm; and a is in a range of approximately 5°-15°, and may be, for example, 10°. The chamfered surface 400 facilitates bending of the rodscrew 100 (FIGS. 1-2) while a guidewire (not shown in FIGS. 3-8) is present within the guidewire path 200 (FIG. 2). In addition, each tab 202 has curved sidewalls 506, which allow rotation and other movement of the bead 104 relative to the other beads with reduced or no interference with the cables 180 (FIG. 1) that extend through the cable through holes 500. A radius of curvature of a sidewall 506, measured from a center of an adjacent cable through hole 500, is in a range of approximately 0.7 mm-1.7 mm, and may be, for example, 1.2 mm. Furthermore, a thickness $t_2$ of each tab 202 is in a range of approximately 1.75 mm-3.75 mm, and may be, for example, 2.75 mm.

The pocket 300, like the tabs 202, has a lollipop shape, with a stem, or neck, 302 and a head 304, and extends, with its full cross-sectional dimensions, all the way through the base 200 of the bead 104. The pocket 300 is configured to receive the tabs 202 of another bead 104 in a manner that allows the two beads to rotate relative to one another so that the rodscrew 100 (FIGS. 1-2) can bend and curve. The pocket neck 302 has a height, $p_1$, from a bottom of the base 200 to a center 306 of the head 304, and has a width $p_2$. In an embodiment, $p_1$ is in a range of approximately 1.5 mm-3.5 mm, and may be, for example, 2.5 mm, and $p_2$ is in a range of approximately 0.6 mm-2.6 mm, and may be, for example, 1.6 mm. And the head 304 has a diameter $p_3$, which, in an embodiment, is in a range of approximately 2.5 mm-4.5 mm, and may be, for example, 3.5 mm.

In an embodiment, each cable through hole 500 has an outer diameter in a range of approximately 0.7 mm-2.7 mm, and may be, for example, 1.7 mm, and has a chamfer 504 with an angle in a range of approximately 0°-40°, and may be, for example, 20°. The chamfers 504 reduce, or eliminate, wear on the cable 180 (FIG. 1) extending through the hole 500 and on the sides of the hole itself as compared to a cable and cable through hole of similar sizes with no through-hole chamfering. And a diameter of a circle 502 on which the centers of the cable through holes 500 lie is, in an embodiment, in a range of approximately 4.0 mm-6.0 mm, and may be, for example, 5.0 mm (the circle 502 is a geometric construct and is not an actual feature of the bead 104).

The central through hole 508 has an outer diameter which is, in an embodiment, in a range of approximately 1.0 mm-3.0 mm, and which may be, for example, 2.0 mm, and has a chamfer 510 with an angle which is, in an embodiment, in a range of approximately 0°-40°, and which may be, for example, 20°. The chamfer 510 reduces, or eliminates, wear on the guidewire (not shown in FIGS. 3-8) and on the sides of the central through hole 508 itself as compared to a guidewire and center through hole of similar sizes with no through-hole chamfering.

Still referring to FIGS. 3-8, in an embodiment, the tabs 202 are configured to provide torque transfer in a range of approximately 2 Newton-meters (Nm)-9 Nm along the length of the rodscrew 100 (FIGS. 1-2), yet the tabs are contoured to prevent interference with the cables 118 (FIG. 1) and guidewire (not shown in FIGS. 3-8) that pass through the beads 104. The curved surface 506 allows for rotation of the bead 104 in all directions with respect to neighboring beads 104 (or transition beads 108, spacer beads 106, or anchor beads 114 of FIG. 1) to obtain a minimum radius of curvature for the rodscrew, which, in an embodiment, is in a range of approximately 50 mm-80 mm, and may be, for example, 65 mm, per FIGS. 1 and 2, without interfering with the cables 180. In an embodiment, a 65 mm bend or curve radius is approximately the tightest radius achievable by the rodscrew 100. Furthermore, the chambered surface 400 of the tabs 202 is at, for example, an angle $\alpha$ of 10° to allow passage of the guidewire (not shown in FIGS. 3-8) at the tightest radius of curvature of, e.g., 65 mm, of the rodscrew 100. The tabs 202 are as long as possible (2.75 mm, for example) from the outer periphery of the base 200 with, e.g., a diameter $b_2$=8.0 mm, to a tab inner surface 408 to allow for relatively high, to maximum, torque transfer and relatively high, to maximum, engagement of the beads 104 to prevent separation of the beads while the rodscrew 100 is under torque and is configured in its tightest radius of curvature yet still allows passage of the central guidewire. The "lollipop" shape of the tabs 202 configure the tabs for engagement with pocket surfaces 700 and 702 to transmit a relatively large torque while allowing full movement of the rodscrew 100 in all directions to obtain, during a rodscrew-implant procedure, any curvature within the capability of the rodscrew.

The pocket 300 runs along the diameter of the bead 104, and the pocket's lollipop shape matches the lollipop shape of the tabs 202. The width $p_2$ of the pocket neck 302 between pocket surfaces 700 on either side of the pocket is, e.g., 1.6 mm, which is slightly larger than the width $n_2$, e.g., of 1.4 mm, of the tab neck 206 and, therefore, which is large enough to allow movement of one bead 104 relative to another bead, but which is not too large to allow the tabs 202 and the pockets 300 to become disconnected during rotation (torque and transmission), bending, and other movements of the rodscrew 100 (FIGS. 1 and 2). Furthermore, the diameter $p_3$ of the pocket head 304 is, e.g., 3.5 mm, which is larger than the diameter $h_1$, e.g., of 2.6 mm, of the tab head 208 and, therefore, which is large enough to allow movement of one bead 104 relative to another bead, but which is not too large to allow the tab heads 208 and the pocket heads 304 to become disconnected during rotation, bending, and other movements of the rodscrew 100 (FIGS. 1 and 2). Moreover, a pocket surface 702, which acts a pocket bridge, is configured to hold a pocket corner 704 in place as it resists being pried open by the tab 202 of a connected bead 104 during torque transmission. Said another way, the pocket surfaces 700 and 702 fully enclose each cable opening 500 near the bottom of the base 200 to strengthen the respective corner 704, and to prevent torque that the rodscrew 100 experiences during implantation and extraction from prying away the corner and from potentially allowing the pocket 300 to disengage a previously engaged tab head 208.

The cable through holes 500 are configured to allow free axial movement of the cables 118 and beads 104 with respect to each other while the rodscrew 100 (FIGS. 1 and 2) is unlocked and, therefore, is in a flexible configuration. However, the cable through holes 500 are not so large that they compromise the stiffness of the rodscrew 100 while the rodscrew is locked in the ridged configuration. In an embodiment, the cable through holes 500 have a diameter of, e.g., 1.702 mm, and each cable 118 has a diameter of, e.g., 1.65 mm.

Furthermore, the cable through holes 500 each have a respective, e.g., 20°, chamfers 504 on both the tab end (e.g., "top" end) and the opposite end (e.g., "bottom" end) of the bead base 200. The chamfers 504 are configured to prevent wear between the bead 104 and the corresponding cable 118 (FIG. 2) while the rodscrew 100 (FIGS. 1 and 2) is curved (see FIGS. 9 and 10). In an embodiment, the chamfers 504 are just large enough to help prevent wear, but not too big to render the base wall too thin in the pocket region 702. As described above, region 702 is large enough to prevent prying open of pocket corner 704 by the tab 202 of an engaged other body bead 104 during a torque transmission (e.g., during an implantation procedure or during an extraction procedure involving the rodscrew 100).

Still referring to FIGS. 3-8, a goal of an embodiment is to maximize the torque capability of a body bead 104 for a given height $b_1$ and diameter $b_2$ of the base 200 while minimizing the bend radius of a rodscrew (e.g., the rodscrew 100 of FIGS. 1 and 2) having a body 102 formed by the beads 104; for example, such an embodiment can yield a body bead that can withstand torque in a range of approximately 2 to 9 Nm and above. Referring to FIG. 5, to achieve this goal, in an embodiment, for given diameters of the through holes 500 and 508, a designer constructs the tab 202 so that the footprint of the tab utilizes a relatively large portion, to all, of a region 512 at the top of the base 200 bordered by the central through hole 508 and two adjacent cable through holes 500. Furthermore, referring to FIG. 4, the designer maximizes the size of the pocket 300 for the given torque goal. Next, the designer configures the tab 202 to have the same or similar cross-sectional shape as the pocket 300, but reducing the cross-sectional dimensions of the tab (relative to the cross-sectional dimensions of the pocket) enough to achieve the given minimum bend radius for the rodscrew. Then, the designer constructs the chamfered and curved surfaces 400, 504, 506, and 510 so that the rodscrew can achieve the given minimum bend radius.

Still referring to FIGS. 3-8, alternate embodiments of the body bead 104 are contemplated. For example, there may be more or fewer than four cable through holes 500, and the tabs 202 and pockets 300 may have shapes other than a lollipop shape. Furthermore, the footprint of the tabs 202 may occupy significantly less than the area of the region 512. In addition, the base 200 may have a shape other than cylindrical. Moreover, embodiments described in conjunction with FIGS. 1-2 and 9-39 may be applicable to the body bead 104 of FIGS. 3-8.

Figure 9:
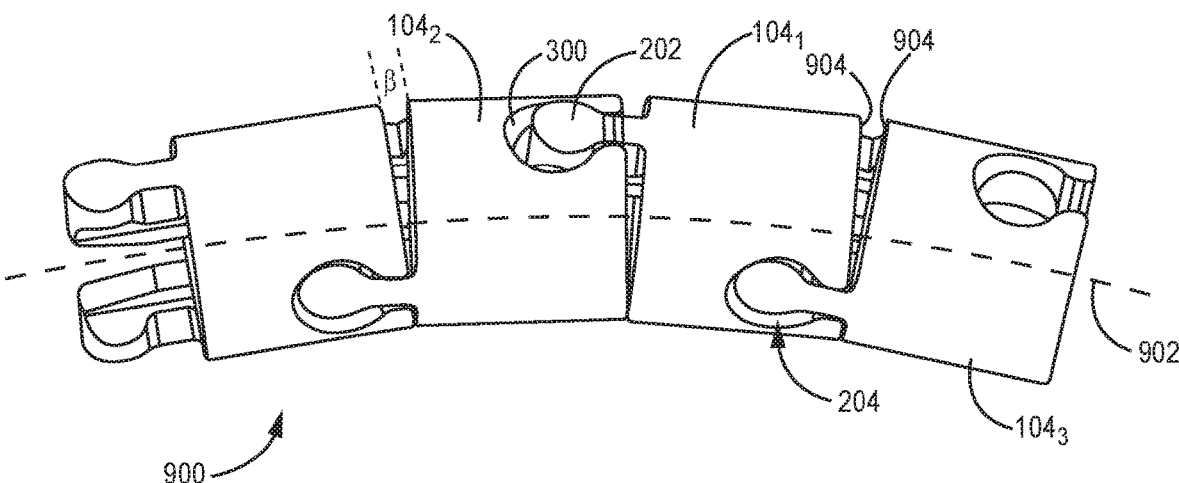
FIG. 9 is a side view of a portion of the body of a rodscrew formed by body beads that are each the same as, or similar to, the body bead of FIGS. 3-8 while the rodscrew is curved, according to an embodiment.

FIG. 9 is a side view of a portion 900 of the body 102 of a rodscrew 100 of FIGS. 1 and 2 formed by body beads 104 of FIGS. 3-8 while the rodscrew is in a curved configuration, according to an embodiment.

Figure 10:
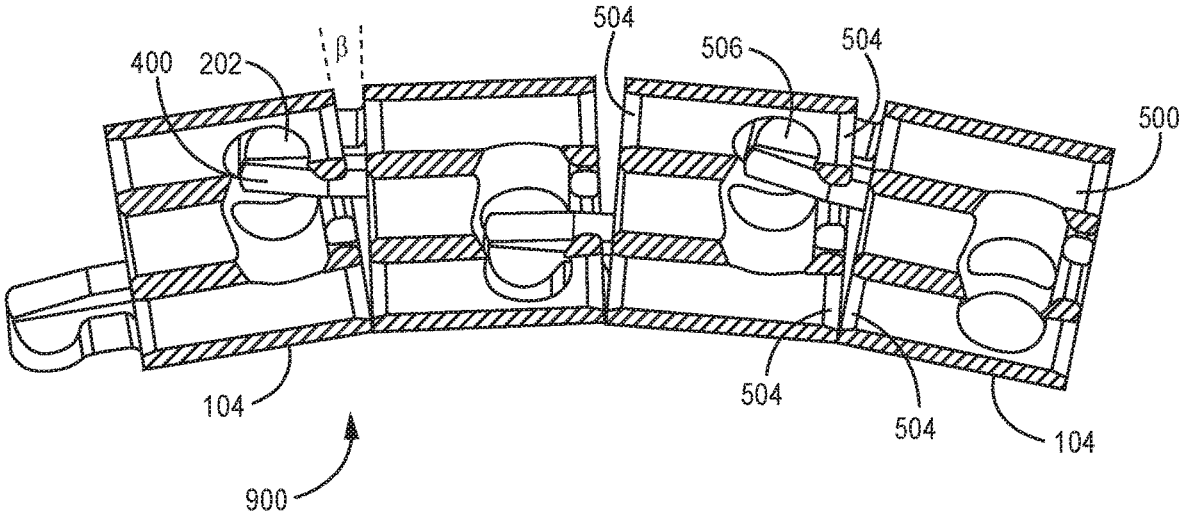
FIG. 10 is a cross-sectional view of the portion of the rodscrew of FIG. 9, according to an embodiment.

FIG. 10 is a cross section of the portion 900 of the rodscrew body of FIG. 9, according to an embodiment.

Referring to FIG. 9, four body beads 104 are interconnected without the cables 118 (FIG. 1) to illustrate the bending capability of the rodscrew, according to an embodiment. The cables 118 are not required to provide torque transmission from bead 104 to bead 104, but the cables typically hold all the beads together in the full rodscrew 100 (FIGS. 1 and 2). The tab 202 of body bead 104₁ interlinks with the pocket 300 of the succeeding (to the left in FIG. 9) body bead 104₂. To rotate the rodscrew 100 completely around its central axis 902 while holding a relatively tight radius of curvature, as it would being screwed (rotated) into or out of a bone (not shown in FIG. 9) during insertion or extraction of the rodscrew, the beads 104 are allowed to rotate with respect to each other and can rotate, for example, along the outer edges 904 of the beads 104₁ and 104₃. For the rodscrew 100 to achieve a tight radius of curvature of, e.g., 65 mm, the end surfaces of the beads 104 circumscribed by the edges 904 are configured to rotate while forming at least an angle $\beta$ relative to one another, where $\beta$ can be in a range of approximately 5.0°-8.0°, and may be, for example, 6.5°. Furthermore, the tabs 202, and the pockets 300, of the beads 104 are contoured (e.g., rounded tab heads 208 and pocket heads 304) to allow such rotation about the axis 902 at a desired bead-to-bead angulation of $\beta$.

FIG. 10 is the rodscrew-body portion 900 of FIG. 9 in cross section and in which the cable through holes 500 are visible, according to an embodiment. At a maximum allowed angle $\beta$ between the beads 104 to give the tightest radius of curvature achievable by the rodscrew 100 (FIGS. 1 and 2), the, e.g., 20° degree, chamfers 504 on both ends of the bead 104 allow for a continuous passageway for the cables 118 (FIG. 1) to run along the rodscrew without causing excessive wear on the cables with the edges of the cable through holes 500.

Furthermore, as described above in conjunction with FIGS. 3-8, the tab surface 506 is chamfered/contoured to allow for a continuous passageway of the cables 118 (FIG. 1) past the tabs 202 while the rodscrew 100 (FIGS. 1 and 2) is configured in its tightest radius of curvature, e.g., 65 mm. Furthermore, the, e.g., 10° angle of the surface 400 is configured to allow for clear passage of a central guidewire (not shown in FIG. 10) through the rodscrew 100 even while the rodscrew is configured having a curve with the rodscrew's tightest radius of curvature.

Figure 11:
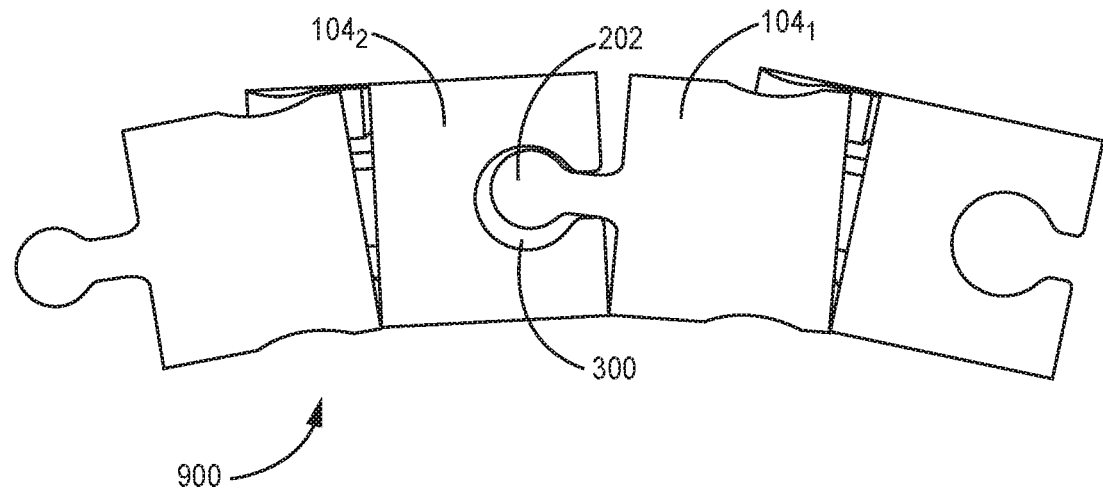
FIG. 11 is a side view of the portion of the rodscrew of FIGS. 9-10 in an orientation different than the orientation show in FIG. 9, according to an embodiment.

FIG. 11 is a side view of the rodscrew-body portion 900 of FIGS. 9-10 in an orientation other than shown in FIGS. 9-10, according to an embodiment.

Figure 12:
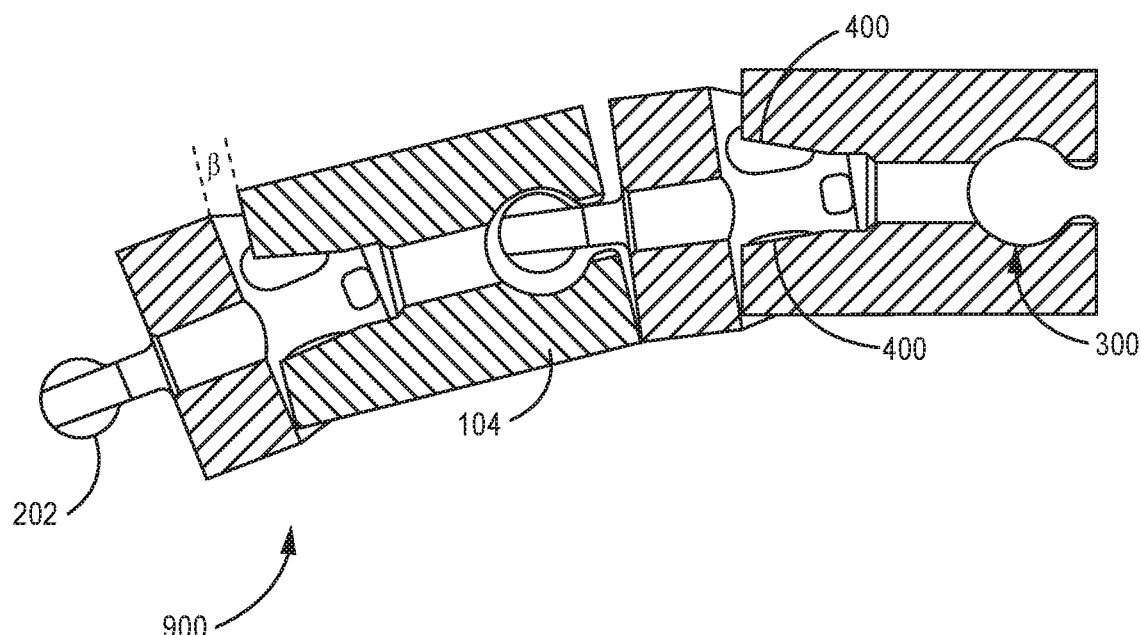
FIG. 12 is a cross-sectional view of the portion of the rodscrew of FIGS. 9-11 in yet another orientation, according to an embodiment.

FIG. 12 is a cross-sectional view of the rodscrew-body portion 900 of FIG. 11, according to an embodiment.

Referring to FIG. 11, four main-body beads 104 are interconnected without the cables 118 (FIG. 1), and the tab 202 of a main body bead 104₁ interlinks with the pocket 300 of another main body bead 104₂.

Referring to FIG. 12, chamfered tab surfaces 400 are each at an angle, e.g., of 10° degrees, sufficient to allow for a continuous passageway of the guidewire (not shown in FIG. 12) while the beads 104 are at a maximum angle β relative to one another at a tightest achievable radius of curvature, e.g., 65 mm, for the rodscrew 100 (FIGS. 1 and 2).

FIG. 13 is a plan view of the rodscrew-body portion 900 of FIGS. 9-12 curved in a relatively tight radius of curvature in a plane orthogonal to the plane of FIG. 13 and in a direction into the page of FIG. 13, according to an embodiment.

FIG. 14 is a plan view of the rodscrew-body portion 900 of FIGS. 9-13 curved in the same radius of curvature as in FIG. 13 in a plane orthogonal to the plane of FIG. 14 and in a direction out from the page of FIG. 14, according to an embodiment.

Referring to FIGS. 13-14, the described orientation of the beads 104 incudes a suitable sizing of the tab 202 of a main-body bead $104_1$ and of the pocket 300 of main-body bead $104_2$.

Referring to FIG. 13, in this orientation example, the tab 202 is as large as possible to fit inside the pocket 300 and to allow for a maximum angle β of, e.g., 6.5°, between the beads 104 to create a tightest radius of curvature, e.g., 65 mm, for the rodscrew 100 (FIGS. 1-2). For example, the neck 206 of the tab 202 is just touching the neck 302 of the pocket 300, and the head 208 of the tab is just touching head 304 of the pocket. This touching engagement of the tab 202 with the pocket 300 stops the movement of the body beads 104 relative to one another, holds the beads together so that they do not separate along the main axis of 902 (FIG. 9) of the rodscrew 100, and occurs while the rodscrew is configured in a curve having the tightest radius of curvature that the rodscrew is configured to achieve.

Referring to FIG. 14, the head 208 of the tab 202 is close to touching a top end 1400 of the head 304 of the pocket 300 opposite the neck 302 of the pocket. The small amount of clearance between the top end 1400 of the pocket head 304 and the tab head 208 allows for the tab 202 to be a large as possible but without interfering with the ability of the body beads 104 to attain the tightest radius of curvature for which the rodscrew 100 (FIGS. 1 and 2) is configured, according to an embodiment.

Referring to FIGS. 3-14, alternate embodiments of the body beads 104 are contemplated. For example, although ranges of absolute dimensions of components of a bead 104 are described, each component also, or instead, can be described in terms of its dimensions relative to the dimensions of another component over a range of that includes the above-described range of approximate dimensions. For example, the height $n_1$ of a tab 202 can be described as being in a range of approximately one fourth to three fourths the height $b_1$ of the base 200; that is, the range of $n_1$ is approximately $\frac{1}{4}b_1 \le n_1 \le \frac{3}{4}b_1$. Furthermore, the components of a bead 104 can have suitable dimensions and shapes other than the dimensions and shapes described. Moreover, embodiments described in conjunction with FIGS. 1-2 and 15-39 may be applicable to the body beads 104 of FIGS. 3-14.

FIG. 15 is a plan view of a rodscrew 1500, which is similar to the rodscrew 100 of FIGS. 1 and 2, and which includes body beads 104 of FIGS. 3-14 that are compressed together, according to an embodiment.

FIG. 16 is a plan view of the rodscrew 1500 of FIG. 15 with the body beads 104 pulled apart, according to an embodiment.

Figure 17:
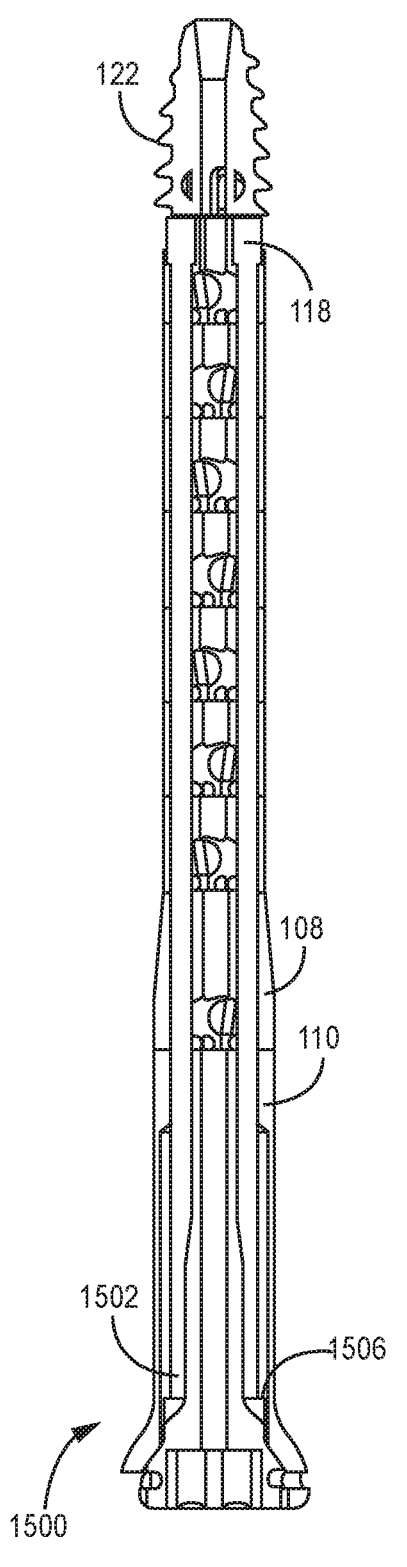
FIGS. 17-18 are cross-sectional views of the rodscrews of FIGS. 15 and 16, respectively, according to an embodiment.
Figure 18:
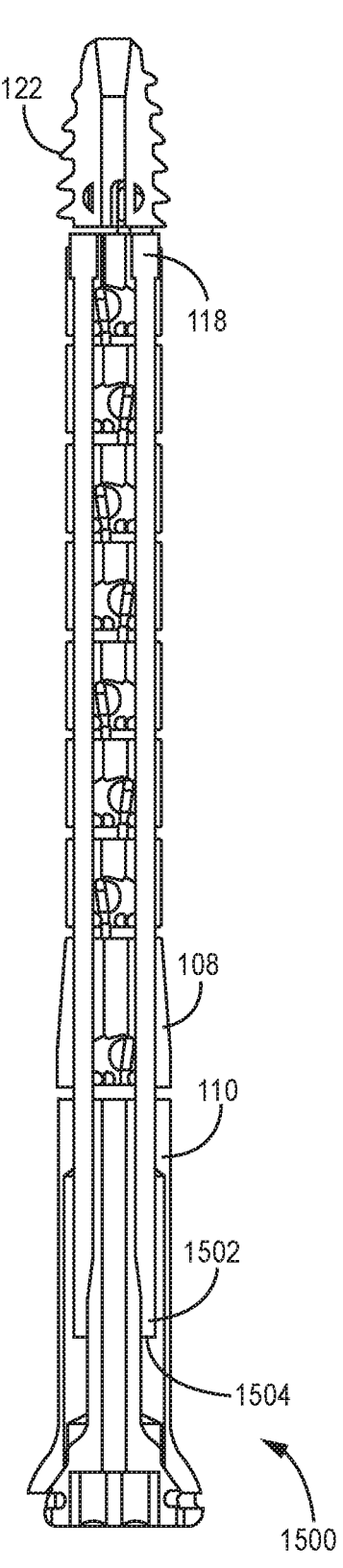

FIGS. 17-18 are cross-sectional views of the rodscrew 1500 of FIGS. 15 and 16, respectively, according to an embodiment.

Referring to FIGS. 15-18, the cables 118 and end caps 120 are secured in the anchor bead 114 cable bores by welding, crimping, or other permanent fixation method. The cables 118 extend the length of the rodscrew 1500, from the anchor bead 114 to the proximal end 110. The cables 118 are not fixed securely at the proximal end 110 while the rodscrew 1500 is unlocked and flexible. This is the state that the rodscrew 1500 typically has while a surgeon is screwing, or otherwise urging, the rodscrew into and through the intramedullary space of a fractured bone during an implantation procedure, or while the surgeon is screwing, or otherwise pulling, the rodscrew out from the intramedullary space during an extraction procedure. In an embodiment, the cables 118 do not extend into the distal end 122. But in another embodiment, the cables 118 are permanently fixed within the distal end 122 instead of in the anchor bead 114 and extend the length of the rodscrew 1500 to the proximal end 110.

One can press the body beads 104 together as shown in FIGS. 15 and 17 such that the end faces of all the body beads meet to configure the rodscrew 1500 to have a shortest overall length in a straight configuration (e.g., while the rodscrew is straight and not curved). The end faces of the bead base 200 (e.g., FIG. 3) are flat, so when the beads 104 are pushed together the entire surface of one end face is, at least ideally, in contact with approximately the entire surface of the neighboring bead's end face.

In contrast, one can pull the body beads 104 apart as shown in FIGS. 16 and 18 such that the interference of the bead tabs 202 and pockets 300 prevent the rodscrew 1500 from lengthening to more than a maximum overall length (in a straight configuration), and, therefore, from pulling apart, according to an embodiment. The maximum overall length for the rodscrew 1500 device depends on the number of beads 104, 106 (optional and not shown in FIGS. 15-18), 108, and 114 that the rodscrew includes. As shown in FIG. 18, the cables 118 are long enough to accommodate the longest overall length that the rodscrew 1500 can have while pulled apart without coming out of the distal end 122 or out of the proximal end 110. The proximal ends 1502 of the cables 180, while the rodscrew 1500 is pulled apart, are at the location 1504 shown in FIG. 18. The cables 118 also are short enough to accommodate the shortest possible length of the rodscrew 1500, as shown in FIG. 17, while all the beads 104, 106, 108, and 114 are pushed together without hitting up against an internal end wall of the proximal end 110. The ends 1502 of the cables 118 while pushed together are at a location 1506 for the rodscrew length shown.

While the body beads 104 are pushed together as shown in FIGS. 15 and 17, the location 1506 is the farthest proximal distance that the cables 118 extend into the proximal end 110. As the rodscrew 1500 is bent or the beads 104, 108, 106 (optional and not shown in FIGS. 15-18) and 114 are forced apart, the proximal ends 1502 of the cables 118 effectively travel distally within the proximal end 110. This effective travel occurs because any change of the beads 104, 106, 108, and 114 away from a completely pushed together configuration forms a gap between each pair of the bead end surfaces and moves the beads along the length of the cables 118. Said another way, if the distal ends (the locations of the end caps 120) of the cables 118 are seen as fixed in space as they are in the anchor bead 114, then all the other beads can be seen as moving along the lengths of the cables as the rodscrew 1500 bends and the beads 104, 106. 108, and 114 pull apart. This separating of the beads 104, 106, 108, and 114 results in the proximal end 110 moving away from the fixed (at least in a relative sense) distal end 122 by sliding axially along the cables 118.

While a surgeon (not shown in FIGS. 15-18) inserts the rodscrew 1500, e.g., into the intramedullary region of a fractured bone, the surgeon attaches an inserter/extractor instrument or tool (not shown in FIGS. 15-18) to the proximal end 110, and, as he/she turns the instrument, the proximal end turns the transition bead 108, which turns the main-body beads 104 and spacer beads 106 (if present), and this transfer of torque continues along the length of the rodscrew to the threaded distal end 122. If the rodscrew 1500 is configured to be used as a lag screw across the fracture site in a bone, the beads 104, 108, and 114 can spread apart as needed to apply tension across the fracture site. To extract the rodscrew 1500, a surgeon reattaches the inserter/extractor instrument to the proximal end 110 and, as the surgeon turns the proximal end, the beads 104, 106 (if present), 108, and 114 turn each other until the transferred torque causes the distal end 122 to turn and, therefore, to unscrew from the bone. The surgeon can pull tension on the inserter/extractor and on the proximal end 110, and the beads 104, 106 (if present), 108, and 114 each transfer this tension to the next bead or to the distal end 122, to extract the rodscrew 1500.

Referring to FIGS. 15-18, alternate embodiments of the rodscrew 1500 are contemplated. For example, a spacer bead 106 (FIGS. 1 and 2) can be, other than having a shorter or longer base 200, the same as or similar to the body bead 104. Similarly, a transition bead 108 (FIGS. 1 and 2) can be, other than having a longer base 200, the same as or similar to the body bead 104. Furthermore, the tabs of the proximal end 110 and the tabs and pockets of the anchor bead 114 can be the same as, or similar to, the tabs 202 and the pockets 300, respectively. Moreover, embodiments described in conjunction with FIGS. 1-14 and 19-39 may be applicable to the rodscrew 1500 of FIGS. 15-18.

Referring to FIGS. 3-18, to attach one body bead 104 to another body bead, one slides the tabs 202 of the one body bead into the pocket 300 of the base 200 of the other body bead.

Then, one inserts one or more cables 118 through the cable bores 500 to keep the now-attached body beads 104 from disengaging from one another by sliding apart.

Figure 19:
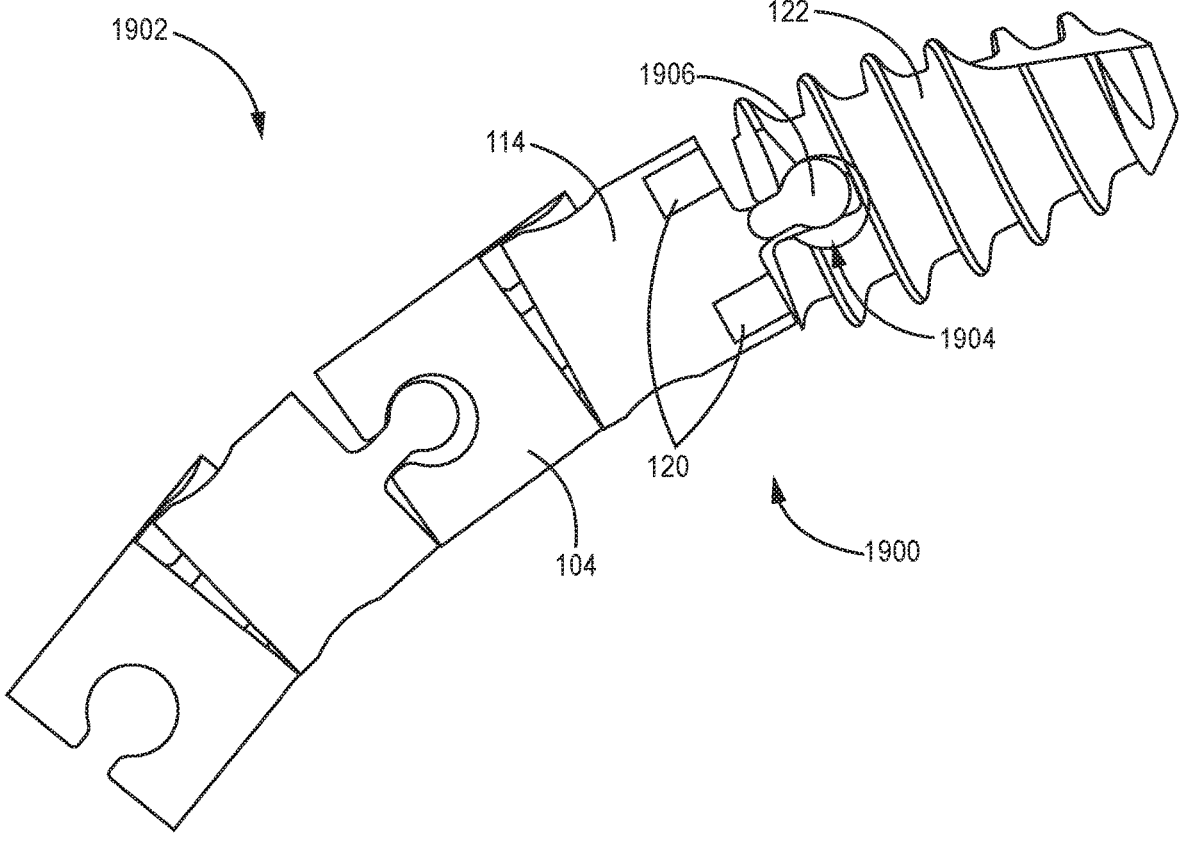
FIG. 19 is a side view of a distal-end portion of a rodscrew including an anchor bead and a distal end, according to an embodiment.

FIG. 19 is a side view of a distal-end portion 1900 of a rodscrew 1902 including a two-piece anchor bead 114 and a distal end 122, according to an embodiment.

FIGS. 20-23 are views of the distal-end portion 1900 of the rodscrew 1902 of FIG. 19 in respective states of assembly, according to an embodiment.

FIG. 24 is an exploded view of the distal-end portion 1900 of the rodscrew 1902 of FIGS. 19-23, according to an embodiment.

Referring to FIG. 19, because, in an embodiment, a pocket 1904 of the distal end 122 does not extend, with its full cross-sectional dimensions, from one side of the distal end to the other side of the distal end, one cannot slide the tabs 1906 of the anchor bead 114 into the pocket as described above for coupling one body bead 104 to another body bead (the tabs 1906 may be similar to, or the same as, the tabs 202 of the body beads 104 as described above in conjunction with FIGS. 3-8).

As described above, the cable caps 120 are anchored in the anchor bead 114 such that the cables 118 (FIG. 2) do not extend into the distal end 122.

Because the cables 118 (FIG. 2) do not extend into the distal end 122, if the pocket 1904 were to extend, with its full cross-sectional dimensions, from one side of the distal end to the other side of the distal end, the distal end could slide off the anchor bead 114.

Configuring the pocket 1904 so that it does not include its full cross-sectional dimensions from one side of the distal end 122 to the other side of the distal end prevents the distal end from sliding off of the anchor bead 114.

But such a configuration of the pocket 1904 does not allow attaching the distal end 122 to the anchor bead 114 by sliding the pocket of the distal end over the tabs 1906 of the anchor bead.

To allow attachment of the distal end 122 to the anchor bead 114 during assembly of the rodscrew 1902, the anchor bead includes two separate halves 1908 and 1910.

Figures 20, 21, 22:
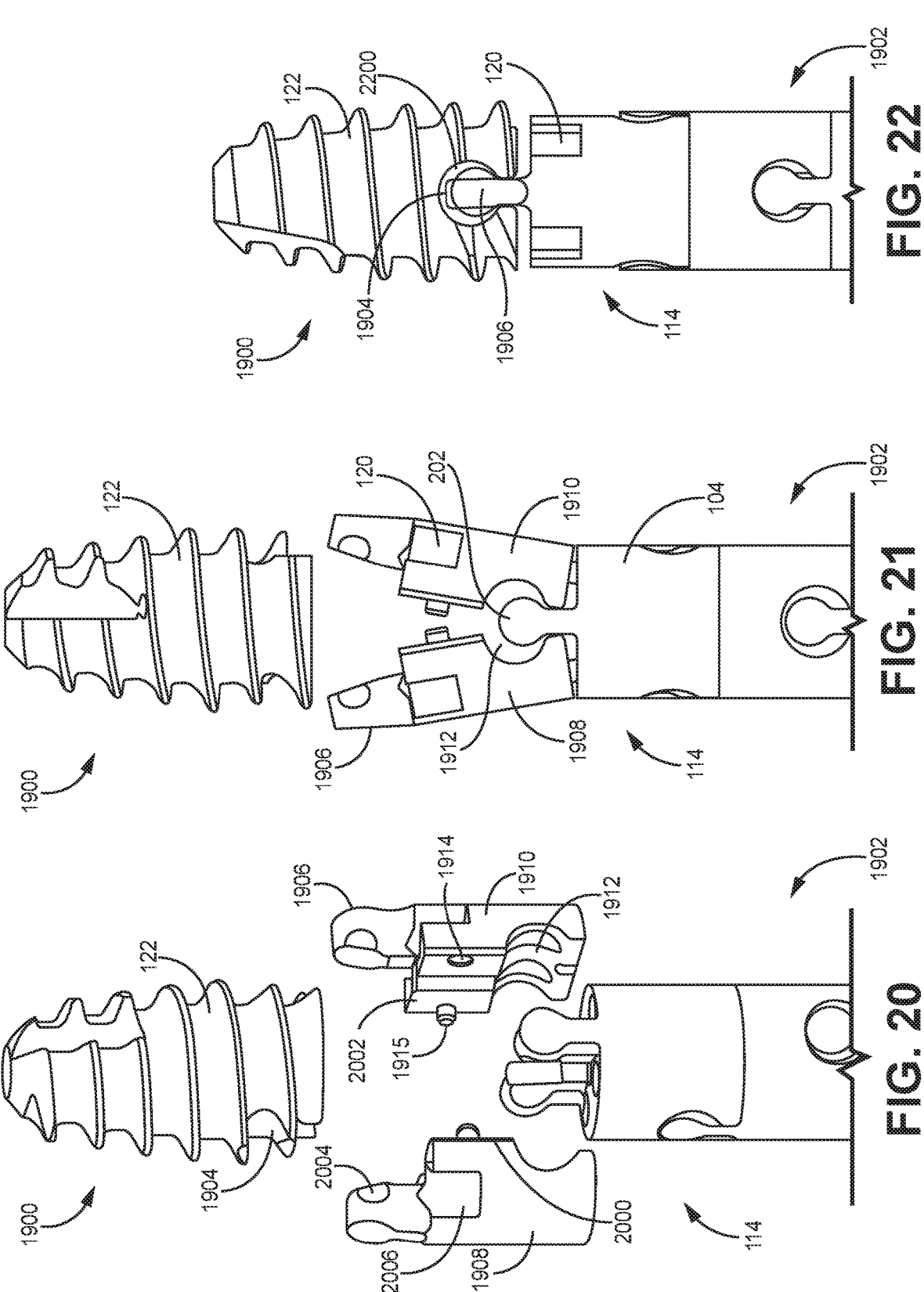

Referring to FIGS. 20-21, during assembly of the rodscrew 1902, one inserts the cables 118 (not shown in FIGS. 20-21) into the cable bores of the anchor bead 114, and attaches (e.g., by crimping, welding, or adhesive) the end caps 120 to the anchor bead, while the halves 1908 and 1910 are unattached to one another.

Then, one moves the two halves 1908 and 1910 together such that a pocket 1912 is formed about the tabs 202 of the preceding body bead 104, and such that tabs 1906 of the anchor bead 114 respectively engage the two ends of the pocket 1904 of the distal end 122. Each half 1908 and 1910 of the anchor bead 114 includes a respective alignment pin 1915 and an alignment receptacle 1914 to help one properly align and engage the two halves of the anchor bead.

After the two halves 1908 and 1910 of the anchor bead 114 are properly aligned and engaged such that the alignment pins 1915 are disposed in the respective alignment receptacles 1914, the tabs 202 of the preceding body bead 104 are disposed within the pocket 1912 of the anchor bead 114, and the tabs 1906 of the anchor bead are disposed within the pocket 1904 of the distal end 122, then one fixes the two halves to one another, for example by welding or adhesive.

FIGS. 19, 22, and 23 show respective views of the assembled anchor bead 114 attached to the distal end 122.

Still referring to FIGS. 19-24, the anchor bead 114 and distal end (bead) 122 are attached to the rest of the rodscrew 1902, according to an embodiment. The anchor bead 114 securely holds onto the cables 118 (FIG. 2) via the cable end caps 120. The cable end caps 120 (alternatively the cables 118 themselves) are welded, crimped, or otherwise permanently attached to the anchor bead 114 in cable counterbores 2300. The anchor bead 114 has two anchor-bead halves 1908 and 1910, which typically are identical. The anchor-bead halves 1908 and 1910 are held in place by the pins 1915 and receptacles 1914 (pins and receptacles also called "mating surfaces") and then welded along the outer body edge 2000 or bonded on mating surfaces 2002. When permanently attached, the two anchor-bead halves 1908 and 1910 take a similar, or the same, shape as the main-body beads 104 with tabs 202 and a pocket 300. The tabs 202 on the main-body bead 104 proximal to the anchor bead 114 interconnect with the pocket 1912 of the anchor bead in a manner similar to the manner in which the main-body beads 104 interconnect.

In an embodiment, the created pocket 1912 of the anchor bead 114 is the same shape and size as the pocket 300 in the main-body beads 104. The tabs 1906 of the anchor bead 114 have the same cross-sectional lollipop shape with head and neck the same size as the head and neck of the pockets 300 of the main-body beads 104, but one surface 2004 may not be as large as the corresponding surface 506 of the mainbody-bead tabs 202. In an embodiment, the surface 2004 forms at least a portion of the cable counterbores 2300 in the anchor bead 114, but the surface 2004 is not as large as its counterpart surface 506 on the main-body beads 104 because the anchor-bead tabs 1906 are configured to capture the distal end 122 and, therefore, cannot and do not interfere with the inner wall of the distal end pocket 2200.

As shown in FIG. 21, after the body beads 104 and the cables 118 (not shown in FIG. 21) are assembled, except for the distal end 122, the halves 1908 and 1910 of the anchor bead 114 are tilted open and the distal end 122 is lowered onto the anchor bead 114. The anchor-bead halves 1908 and 1910 are pushed back together, and the distal end 122 is captured as shown in FIGS. 22-23. The distal end 122 has a wall 2200, which extends through the middle of the distal end to prevent the distal end from "coming off" or "sliding off" the end of the rodscrew 1902. The distal end 122 also has a through passage 2400, which allows the distal end to tilt and rotate on the rodscrew 1902 so that the distal end can attain, along with the remainder of the rodscrew, the tightest radius of curvature for which the rodscrew is configured without being blocked, or otherwise hindered, by the anchor-bead tabs 1906 as shown in FIG. 19. As stated above, all beads other than the distal end 122 each have a completely open passage in the bead pocket (e.g., the pocket 300 of each body bead 104); in contrast, the pocket 1904 of the distal end 122 is only partially open.

After the distal end 122 is aligned and engaged with the anchor bead 114, the anchor-bead halves 1908 and 1910 are pressed together and bonded or welded along the outer edges of the two halves to form the single anchor bead 114. The cables 118 (or the cable caps 120) are welded, crimped, bonded, or otherwise secured into the cable counterbores 2006. After the cables 118 are secured into the cable counterbores 2006, the distal end 122 typically cannot be removed, at least not without damaging or destroying the rodscrew 1902.

Still referring to FIGS. 19-24, alternate embodiments of the rodscrew 1902 are contemplated. For example, embodiments described in conjunction with FIGS. 1-18 and 25-39 may be applicable to the rodscrew 1902 of FIGS. 19-24.

FIG. 25 is an isometric view of a rodscrew distal end 2500 having tabs 2502 instead of pockets, according to an embodiment.

FIG. 26 is a side view of the rodscrew distal end 2500 of FIG. 25 and a two-piece anchor bead 2600 having a pocket 2602 configured to engage the tabs 2502, according to an embodiment.

Referring to FIGS. 25-26, the distal end 2500 can be similar to the distal end 122 of FIGS. 1-2 and 15-24 except that the distal end 2500 includes the tabs 2502 instead of a pocket 1904.

Furthermore, the anchor bead 2600 can be similar to the two-piece anchor bead 114 of FIGS. 19-24 except that cable bores 2604 are disposed on a pocket end 2606 of the anchor bead 2600 instead of on a tab end like the cable bores 2006 of FIG. 20 and 2300 of FIG. 23.

The anchor bead 2600 can be assembled and installed into a rodscrew in a manner similar to that described above in conjunction with FIGS. 19-24, except that the pocket 2602 engages the tabs 2502 of the distal end 2500 instead of engaging the tabs 202 of the adjacent body bead 104 (e.g., FIG. 19), and anchor-bead tabs 2608 engage a pocket 300 of the adjacent body bead instead of engaging a pocket of the distal end.

Furthermore, in a rodscrew that includes the distal end 2500 and the anchor bead 2600, the proximal end (not shown in FIGS. 25-26) can be modified to include a pocket instead of tabs like the proximal end 110 of FIG. 1 includes. Alternatively, such a rodscrew can include at least one interface body bead with pockets on both ends, or at least one interface body bead with tabs on both ends.

Still referring to FIGS. 25-26, alternate embodiments of the distal end 2500 and the anchor bead 2600 are contemplated. For example, embodiments described in conjunction with FIGS. 1-24 and 27-39 may be applicable to the distal end 2500 or the anchor bead 2600 of FIGS. 25-26.

Figures 27, 28:
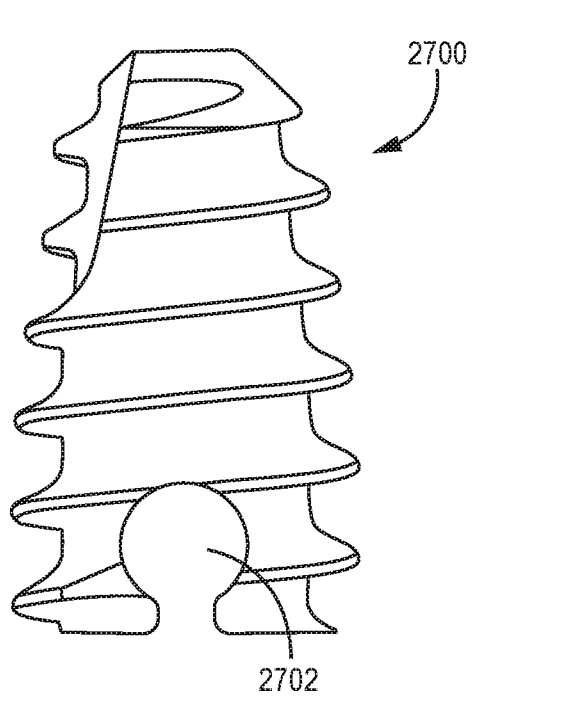
FIG. 27 is a side view of a rodscrew distal end with a full through pocket, according to an embodiment.
FIG. 28 is a perspective view of a rodscrew distal end with the rodscrew cables anchored therein, according to an embodiment.

FIG. 27 is a side view of a distal end 2700 with a through pocket 2702, according to an embodiment. Unlike the pocket 1904 of the distal end 122 of FIGS. 19-24, the pocket 2702 has the same dimensions throughout. But for the pocket 2702, the distal end 2700 can be similar to the distal end 122 of FIGS. 19-24.

Still referring to FIG. 27, alternate embodiments of the distal end 2700 are contemplated. For example, embodiments described in conjunction with FIGS. 1-26 and 28-39 may be applicable to the distal end 2700 of FIG. 27.

FIG. 28 is a perspective view of a distal end 2800 having cable bores 2802 configured for anchoring the cables 118 or the cable end caps 120, according to an embodiment. By allowing the cables 118 or endcaps 120 to be anchored therein, the distal end 2800 can connect directly to a body bead 104 (FIG. 19), and thus allow elimination of all anchor beads 114 (FIGS. 1-2 and 19-24). Because an anchor bead 114 is an extra component, elimination of anchor beads reduces the rodscrew component count and, therefore, can reduce costs for manufacturing the rodscrew components and for assembling the rodscrew. But for the cable bores 2802, the distal end 2800 can be similar to the distal end 122 of FIGS. 19-24 or the distal end 2700 of FIG. 27.

Still referring to FIG. 28, alternate embodiments of the distal end 2800 are contemplated. For example, embodiments described in conjunction with FIGS. 1-27 and 29-39 may be applicable to the distal end 2800 of FIG. 28.

FIG. 29A is a cross-sectional view of a rodscrew distal end 2900 and an anchor bead 2902, which are configured for threaded engagement, according to an embodiment.

FIG. 29B is an isometric view of the rodscrew distal end 2900 and the anchor bead of FIG. 29A.

Figure 29:
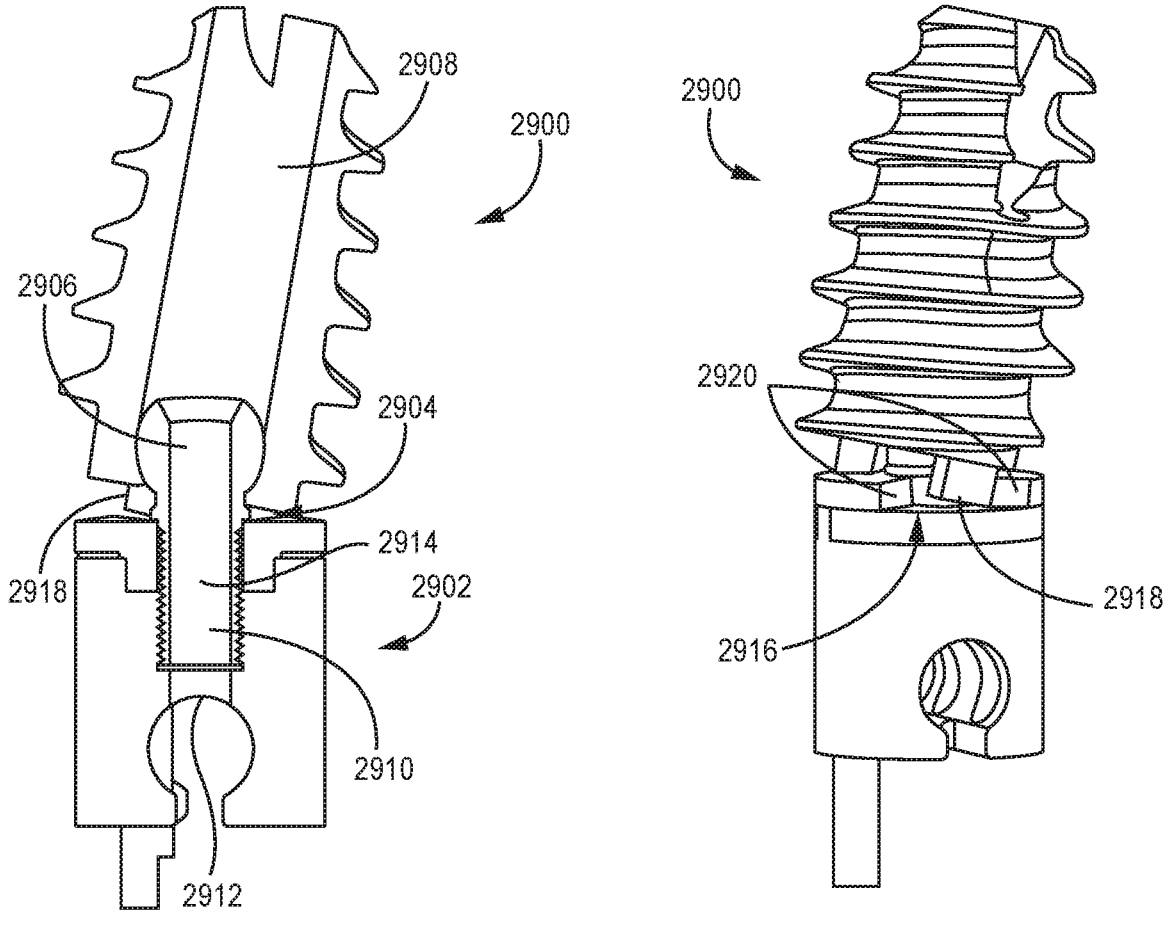
FIG. 29A is a cross-sectional side view of a rodscrew distal end and an anchor bead that are configured for threaded engagement, according to an embodiment.
FIG. 29B is an isometric view of the rodscrew distal end and the anchor bead of FIG. 29A, according to an embodiment.

Referring to FIGS. 29A and 29B, a threaded member 2904 having a head 2906 is inserted through a top of an opening 2908 in the distal end 2900, and a threaded stem 2910, which is narrower than the head, extends from a bottom of the opening of the distal end. The bottom of the opening 2908 is narrower than the top of the opening so that the head 2906 engages the bottom of the opening without passing through it. Also, the head 2906 is shaped (e.g., round) such that the distal end 2900 can pivot about the head at least to an extent that allows a rodscrew (not shown in FIG. 29) that includes the distal end to attain the minimum bend radius for which the rodscrew is configured.

The threaded stem 2910 engages threads in an opening 2912 of the anchor bead 2902, which, but for the lack of tabs and the inclusion of the opening and slots (described below), can be similar to any one of the anchor beads 114 described above in conjunction with FIGS. 1-2 and 19-24).

Furthermore, the threaded member 2904 includes an axial through hole 2914 that runs the length of the member and that is configured to allow the member to pass over a guidewire (not shown in FIGS. 29A and 29B) during a rodscrew implant procedure.

But so that the distal end 2900 rotates in response to a surgeon rotating the rodscrew to which the distal end belongs (e.g., during an implant procedure in which the surgeon is screwing the distal end into a bone, or during an extraction procedure in which the surgeon is unscrewing the distal end from a bone), the anchor bead 2902 can include one or more slots 2916 and the distal end can include one or more tabs 2918 each configured to engage a respective slot. In response to a rotation of the rodscrew, a wall 2920 of a slot 2916 engages the corresponding tab 2918, and, therefore, the slot and tab cooperate to transfer torque from the anchor bead 2902 to the distal end 2900 so that a surgeon can screw the distal end into a bone, or unscrew the distal end from a bone. Furthermore, the slots 2916 and the tabs 2918 are configured so that the distal end can bend with the rodscrew, and does not hinder, or otherwise prevent, the rodscrew from attaining the minimum bend radius for which it is configured.

Still referring to FIGS. 29A-29B, alternate embodiments of the distal end 2900 and anchor bead 2902 are contemplated. For example, embodiments described in conjunction with FIGS. 1-28 and 30-39 may be applicable to the distal end 2900 or the anchor bead 2902 of FIG. 29.

Figure 30:
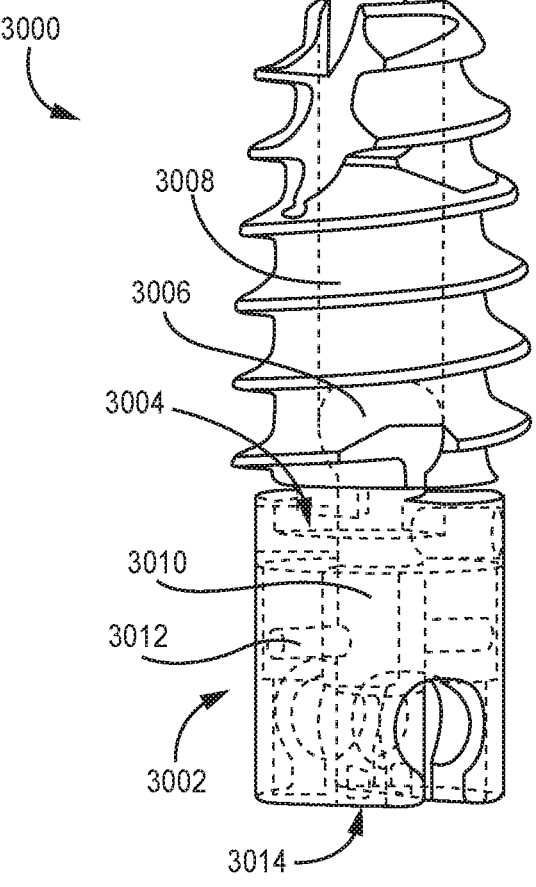
FIG. 30 is a transparent side view of a rodscrew distal end and an anchor bead that are configured for pinned engagement, according to an embodiment.

FIG. 30 is a transparent view of a rodscrew distal end 3000 and an anchor bead 3002 that are configured for pinned engagement, according to an embodiment.

A member 3004 having a head 3006 is inserted through a top of an opening 3008 in the distal end 3000, and a stem 3010, which is narrower than the head, extends from a bottom of the opening of the distal end. The bottom of the opening 3008 is narrower than the top of the opening so that the head 3006 engages the bottom of the opening without passing through it. Also, the head 3006 is shaped (e.g., round) such that the distal end 3000 is configured to pivot about the head 3006 at least to an extent that allows a rodscrew (not shown in FIG. 30) that includes the distal end to attain the minimum bend radius for which the rodscrew is configured.

A pin 3012 secures the stem 3010 in an opening 3014 of the anchor bead 3002, which, but for the lack of tabs and the inclusion of the opening and the pin, can be similar to any one of the anchor beads 114 described above in conjunction with FIGS. 1, 19-24, 26, and 29A-29B.

Furthermore, the member 3004 includes an axial through hole that runs the length of the member and that is configured to allow the member to pass over a guidewire (not shown in FIG. 30) during a rodscrew implant procedure.

But to allow transfer of torque to the distal end 3000 during an implant procedure and an extraction procedure, the distal end and the anchor bead 3002 can include, respectively, tabs and slots that are similar to the tabs 2918 and slots 2916 described above in conjunction with FIGS. 29A and 29B.

Still referring to FIG. 30, alternate embodiments of the distal end 3000 and anchor bead 3002 are contemplated. For example, the stem 3010 may include more than one pin 3012 therethrough to secure the member 3004 to the anchor bead 3002. Furthermore, the anchor bead 3002 may include two halves like the anchor bead 114 of FIGS. 19-24, and the pin 3012 may be configured for installation before the two halves are attached together such that the pin is contained within the anchor bead. Moreover, embodiments described in conjunction with FIGS. 1-29 and 31-39 may be applicable to the distal end 3000 or the anchor bead 3002 of FIG. 30.

Figure 31:
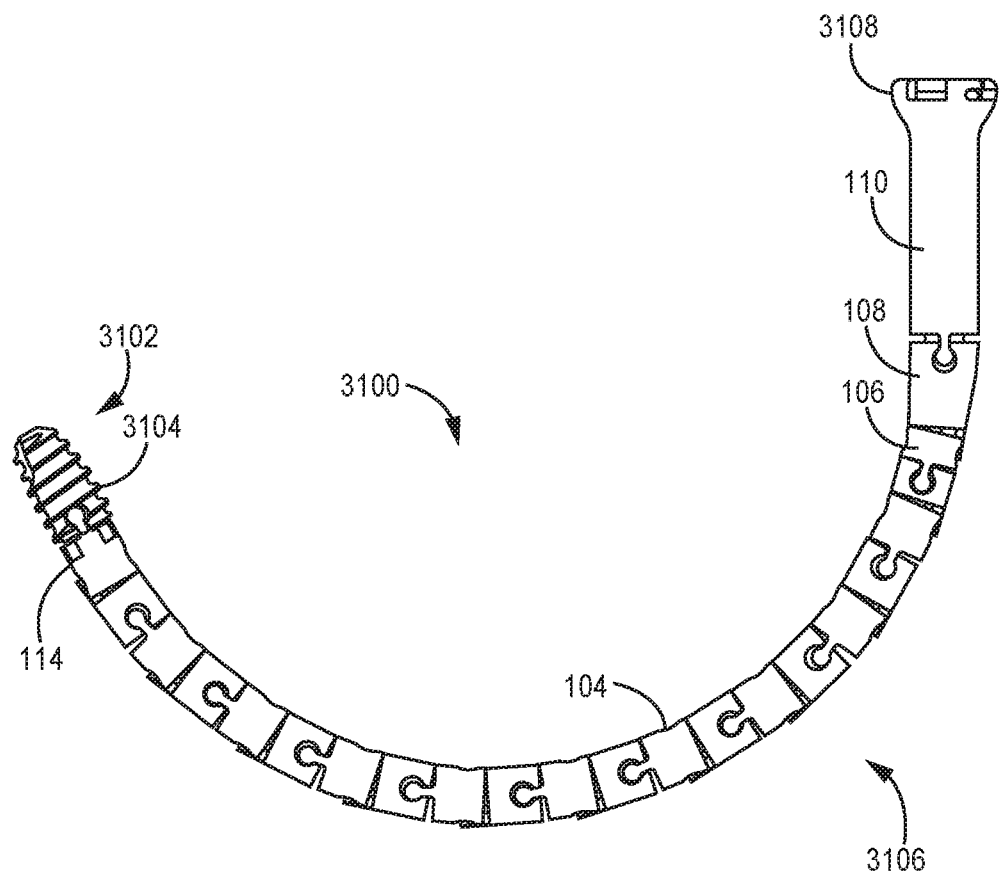
FIG. 31 is an isometric view of a rodscrew that is similar to the rodscrew of FIGS. 1 and 2 but which has a distal end that is no wider than the main, segmented body of the rodscrew, according to an embodiment.

FIG. 31 is an isometric view of a rodscrew 3100, which is similar to the rodscrew 100 of FIGS. 1 and 2 but which has a distal end 3102 having threads 3014, which are no wider than a main, segmented body 3106 of the rodscrew 3100, according to an embodiment.

In more detail, the threads 3104 have a largest diameter that is no greater than the diameters of any of the proximal end 110 (except for a flanged head 3108 of the proximal end), the transition bead 108, the spacer bead 106, the body beads 104, and the anchor bead 114.

Because the threads 3104 of the distal end 3102 are no wider than the rodscrew body 3106, a surgeon (not shown in FIG. 31) can ream, in an intramedullary space of a fractured bone (not shown in FIG. 31), a main intramedullary path that is about the same width as the rodscrew body 3106, and, at the end of the main path, can ream a narrower path extension within which the threads 3104 of the distal end 3102 can engage the bone. Therefore, the distal end 3102 allows a surgeon to hammer, or otherwise to push, the rodscrew 3100 through the main intramedullary path all the way to the intramedullary path extension instead of screwing the rodscrew through the main path; after the tip of the distal end reaches the path extension, the surgeon can screw the distal end into the path extension such that the distal-end threads 3104 secure the rodscrew 3100 to the bone in which the path extension is formed. Furthermore, the main intramedullary path for the rodscrew 3100 can be narrower than the main intramedullary path for the rodscrew 100 (FIGS. 1 and 2). For example, in an embodiment, the threads 122 of the distal end 116 of FIG. 1 have a widest diameter of approximately 9.5 mm, whereas in an embodiment, the threads 3104 of the rodscrew 3100 have a widest diameter of 8.0 mm.

Alternate embodiments of the rodscrew 3100 are contemplated. For example, one or more embodiments described in conjunction with FIGS. 1-30 and 31-39 may be applicable to the rodscrew 3100 or to a procedure for implanting the rodscrew.

Figure 32:
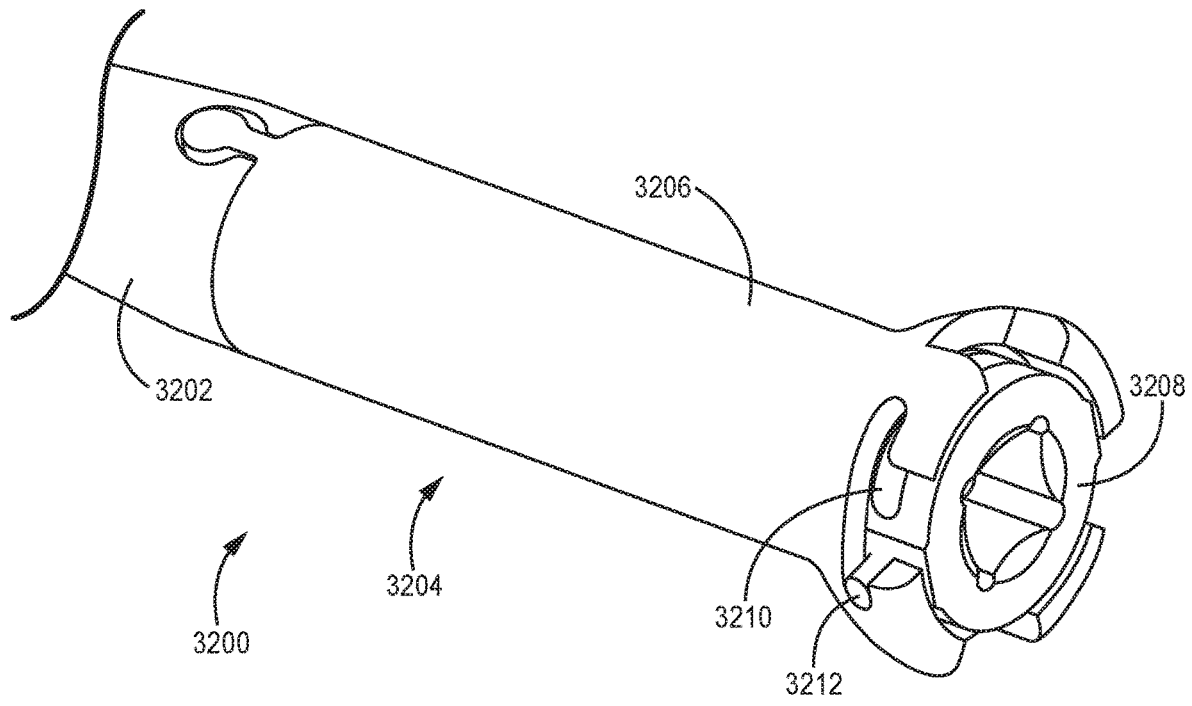
FIG. 32 is an isometric view of a portion of a rodscrew including a proximal anchor bead and a proximal end, according to an embodiment.

FIG. 32 is an isometric view of a portion of a rodscrew 3200 including a transition bead, and a proximal end 3204, according to an embodiment.

Figure 33:
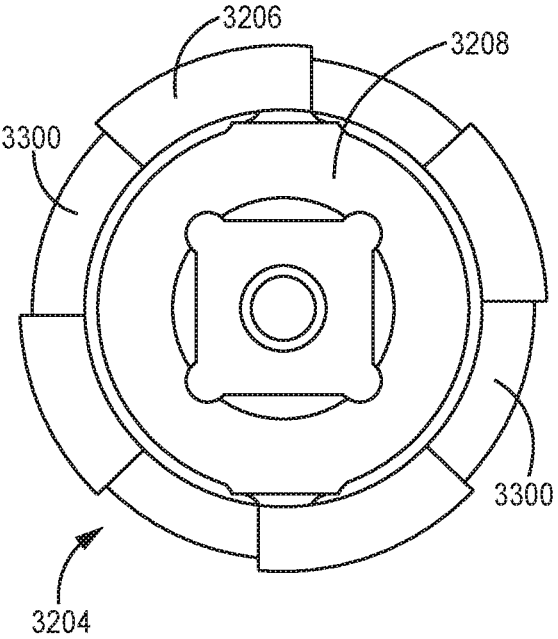
FIG. 33 is an end view of the proximal end of FIG. 32, according to an embodiment.

FIG. 33 is an end view of the proximal end 3204 of the rodscrew 3200 of FIG. 32, according to an embodiment.

Figure 34:
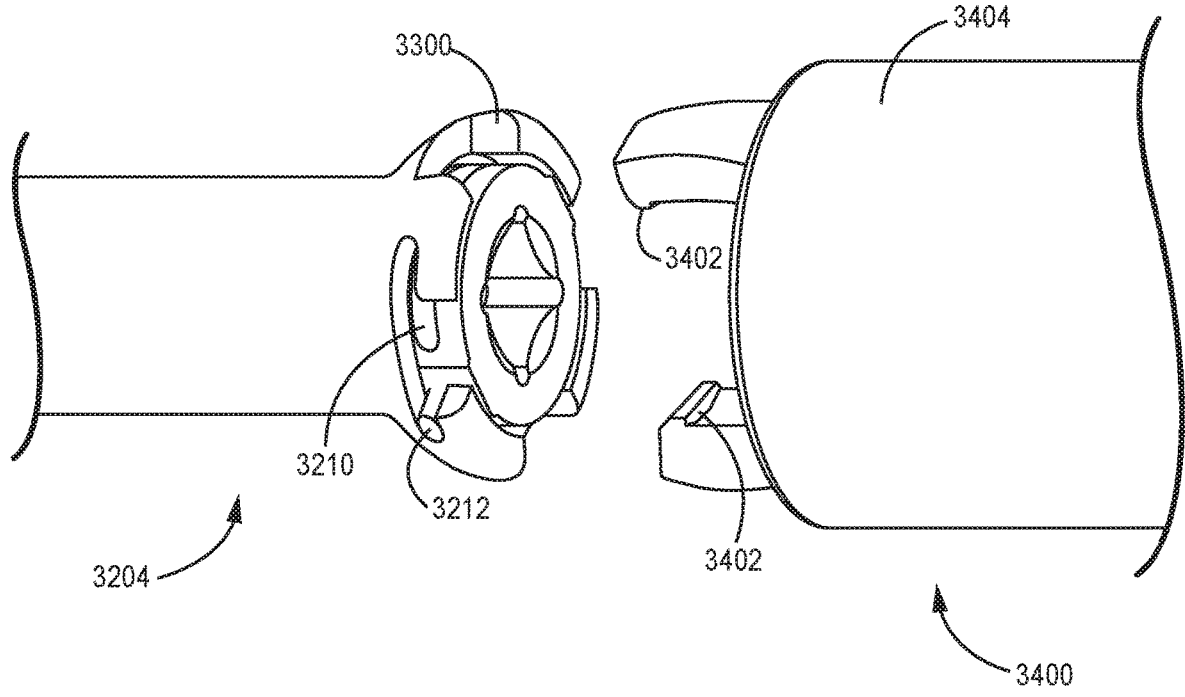
FIG. 34 is an isometric view of the proximal end of FIGS. 32-33 and a tool configured to insert, extract, rotate, lock, and unlock the rodscrew to which the proximal end belongs, and to remove the locking mechanism from within the proximal end, according to an embodiment.

FIG. 34 is an isometric view of the proximal end 3204 of the rodscrew 3200 of FIG. 32, and of a tool 3400 configured to insert, extract, rotate, lock, and unlock the rodscrew, and to remove a locking mechanism from the rodscrew, according to an embodiment.

Figure 35:
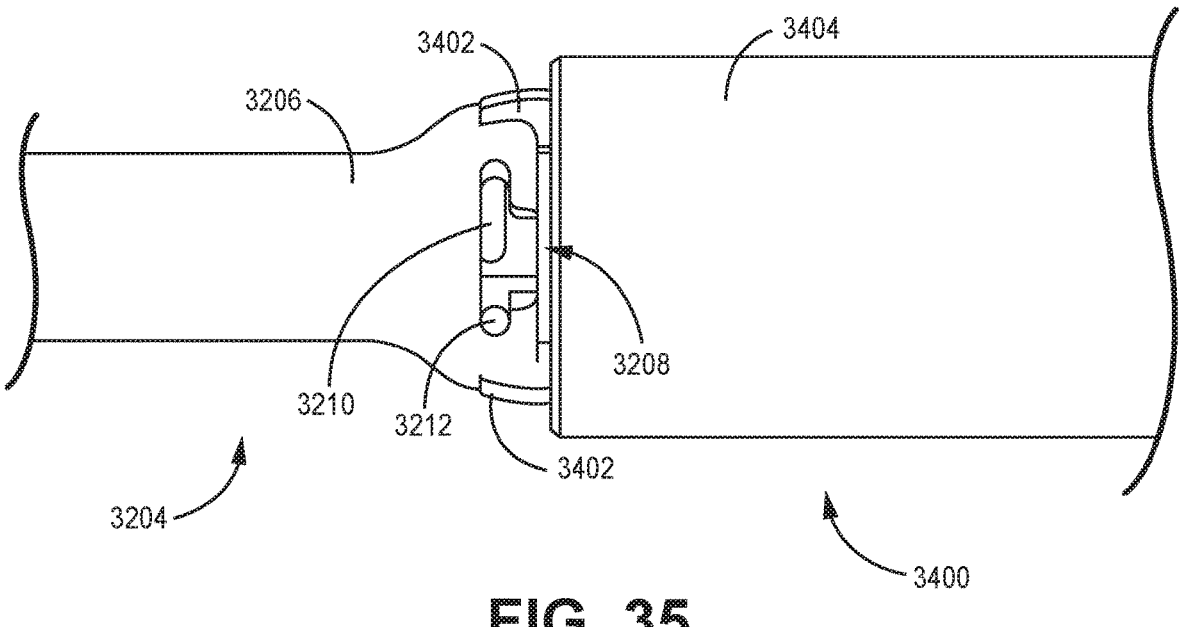
FIG. 35 is a side view of the tool of FIG. 34 engaged with the proximal end of FIG. 34 while the proximal end is in an unlocked configuration, and while the rodscrew to which the proximal end belongs is in a flexible configuration, according to an embodiment.

FIG. 35 is a side view of the tool 3400 of FIG. 34 engaged with the proximal end 3204 of the rodscrew 3200 of FIG. 32 while the proximal end is in an unlocked configuration, and while the rodscrew is in a flexible configuration, according to an embodiment.

Figure 36:
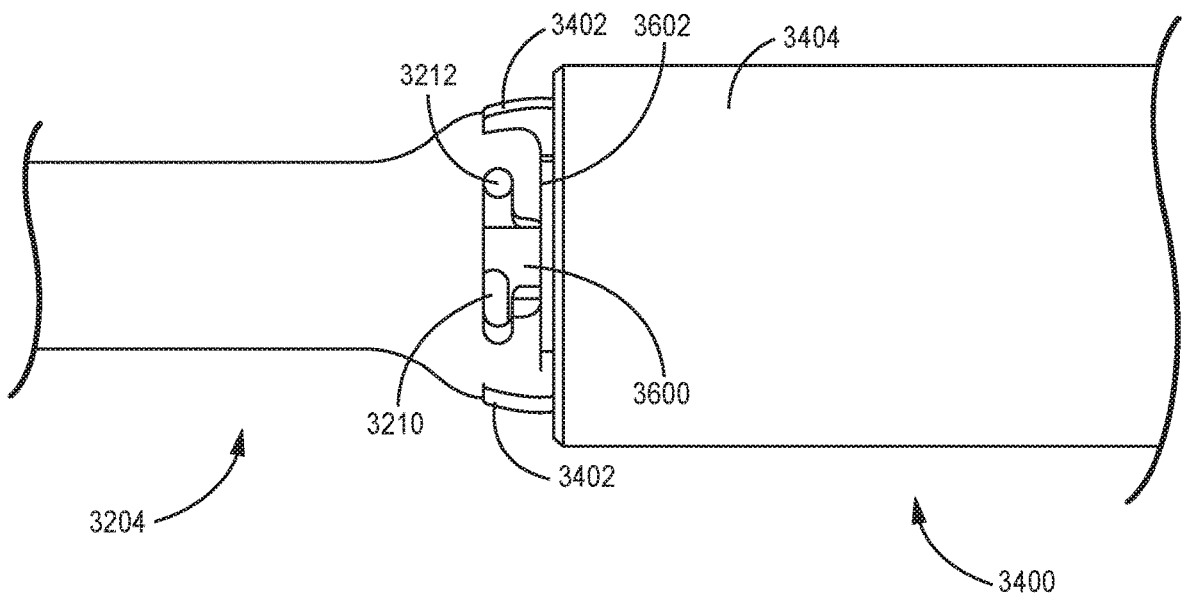
FIG. 36 is a side view of the tool of FIG. 34 engaged with the proximal end of FIG. 34 while the proximal end is in a locked configuration, and while the rodscrew to which the proximal end belongs is in a rigid configuration, according to an embodiment.

FIG. 36 is a side view of the tool 3400 of FIG. 34 engaged with the proximal end 3204 of the rodscrew 3200 of FIG. 32 while the proximal end is in a locked configuration, and while the rodscrew is in a rigid configuration, according to an embodiment.

Referring to FIGS. 32-36, the inserter-extractor tool 3400 attaches to a housing 3206 of the proximal end 3204 to insert the rodscrew 3200 into a bone (not shown in FIGS. 32-36) or to extract (remove) the rodscrew from the bone (extraction is optional), according to an embodiment. The tool 3400 securely holds onto the rodscrew 3200 while allowing an inner proximal lock 3208 of the proximal end 3204 to rotate in order to lock the rodscrew into a rigid configuration (the rodscrew can be straight or curved in the rigid configuration). Tangs 3402 of the tool 3400 are placed into open slots 3300 of the proximal housing 3206. An outer tube 3404 of the tool 3400 rotates to travel down the length of the tool and to press the tangs 3402 inward toward the proximal lock 3208. The ends of the tangs 3402 are captured in a groove 3210 of the proximal lock 3208. When pressed inward enough, the tangs 3402 are locked into the groove 3210 and, therefore, the tool 3400 is securely attached to the rodscrew 3200. The spacing of the groove 3210 and the ends of the tangs 3402 still allows for the proximal lock 3208 to rotate within the housing 3206 of the proximal end 3204.

FIG. 35 shows the tool 3400 engaged with the proximal lock 3208. After the rodscrew 3200 is inserted into the bone (not shown in FIGS. 32-36), the proximal lock 3208 is turned and a pin 3212 rotates in the proximal housing 3206 and the rodscrew becomes rigid. The groove 3210 is long enough to accommodate the inserter tangs 3402 as the lock 3208 rotates within the proximal housing.

The tool 3400 also can be used to the remove the proximal lock 3208 from the proximal housing 3404 if needed. To do this, the proximal lock 3404 is rotated until the pin 3212 is in an open area 3600 between the fully unlocked and locked positions of the pin.

When the pin 3212 is in this in-between position, a thin part of a clamp, tweezers, or something else metallic (none of clamp, tweezers, something else metallic shown in FIGS. 32-36) is placed between an end 3602 of the proximal housing 3206 and the outer tube 3404 of the tool 3400. The outer tube 3404 is then rotated clockwise. As the outer tube 3404 advances, it squeezes down on the piece of metal and the tangs 3402 of the tool 3400 that are captured inside the groove 3210 back the proximal lock 3404 out of the proximal housing 3404.

Still referring to FIGS. 32-36, alternate embodiments of the rodscrew 3200 are contemplated. For example, one or more embodiments described in conjunction with FIGS. 1-31 and 37-39 may be applicable to the rodscrew 3200, a procedure for implanting the rodscrew, a procedure for locking or unlocking the rodscrew, or a procedure for disassembling the rodscrew, for example, a procedure for removing the proximal lock 3208 from the proximal housing 3404.

Figure 37:
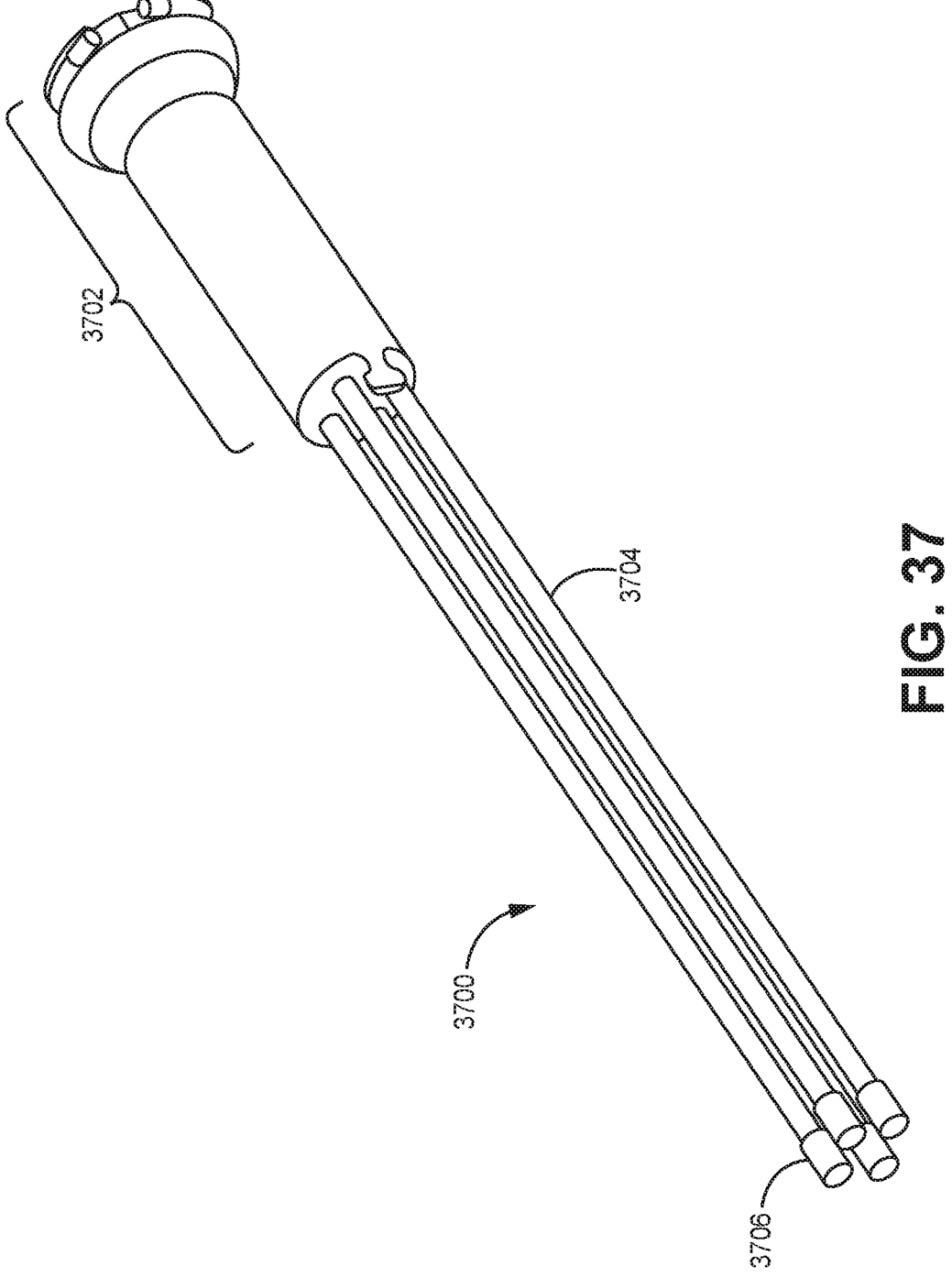
FIG. 37 is an isometric view of a rodscrew, which can be similar to one or more of the rodscrews of FIGS. 1-2, 15-18, and 31, in a straight configuration with the body segments and the distal end omitted, according to an embodiment.

FIG. 37 is an isometric view of a rodscrew 3700, which can be similar to one or more of the rodscrews 100, 1500, and 3100 of FIGS. 1-2, 15-18, and 31, respectively, in a straight configuration with the body segments and the distal end omitted, according to an embodiment.

Figure 38:
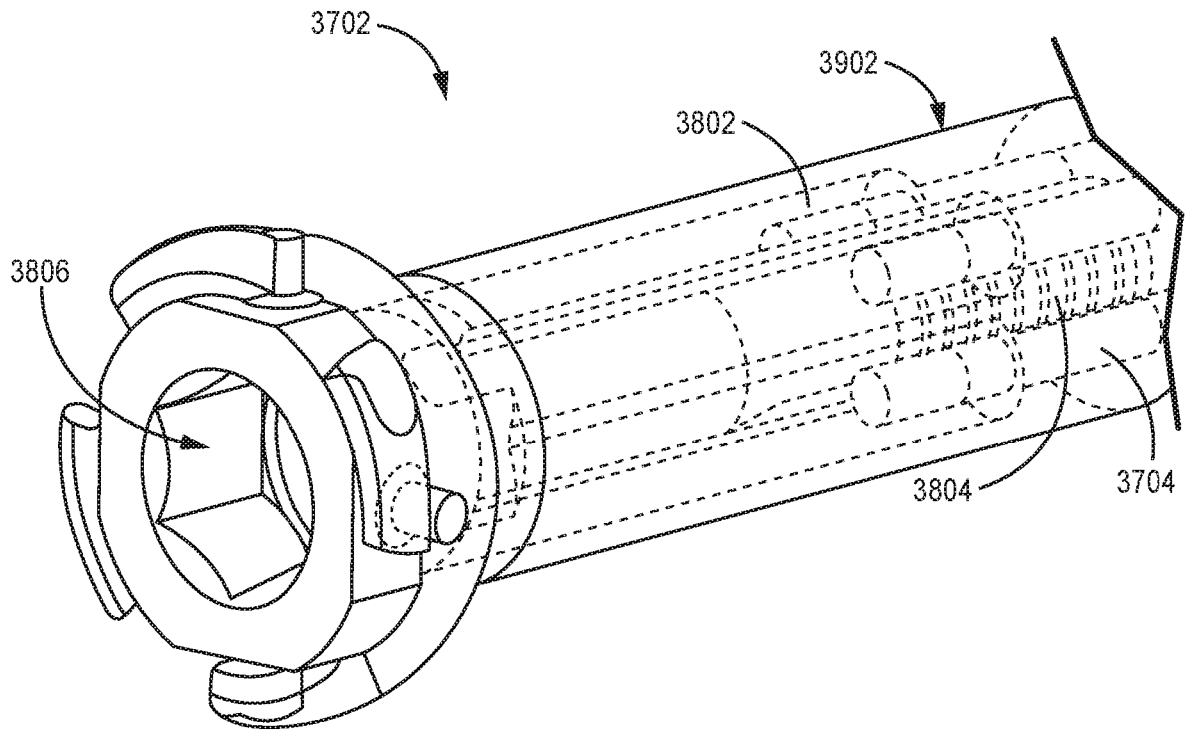
FIG. 38 is a transparent view of the proximal end of the rodscrew of FIG. 37 in an unlocked configuration, according to an embodiment.

FIG. 38 is a transparent view of the proximal end 3702 of the rodscrew 3700 of FIG. 37 in an unlocked configuration, according to an embodiment.

Figure 39:
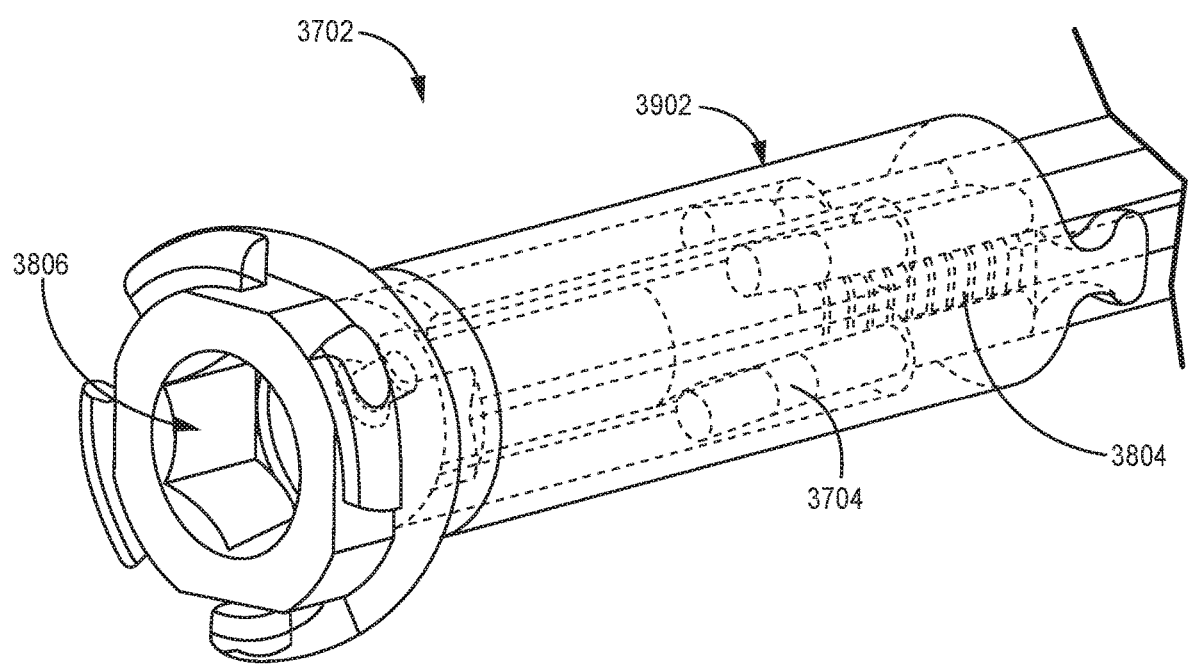
FIG. 39 is a transparent view of the proximal end of the rodscrew of FIG. 37 in a locked configuration, according to an embodiment.

FIG. 39 is a transparent view of the proximal end 3702 of the rodscrew 3700 of FIG. 37 in a locked configuration, according to an embodiment.

Referring to FIG. 37, in addition to a proximal end 3702, which can be the same as, or similar to, the proximal ends 110 of FIGS. 1-2, 15-18, and 31 and as described in WO 2018/067888, which is incorporated by reference.

The rodscrew 3700 includes cables, for example, four cables, 3704, each of which extends from the proximal end, through a respective cable bore of each of the beads (neither cable bores nor beads not shown in FIG. 37) that form a body of the rodscrew, to an anchor bead (not shown in FIG. 37). In an embodiment, the cables 3704 can be similar to the cables 118 of FIG. 1, the cable bores can be similar to cable bores 500 of, e.g., FIG. 5, the beads can be similar to one or more of the beads 104, 106, and 108 of, e.g., FIG. 1, and the anchor bead can be similar to the anchor bead 114 of, e.g., FIG. 1.

And each of the cables 304 includes, at its distal end, a respective cable cap 3706, which can be compression fitted onto the end of the cable and which can be similar to the cable caps 120 of, e.g., FIG. 1. The cable cap 3706 engages a respective cable slot in the anchor bead, for example, as shown in conjunction with the anchor bead 114 and cable caps 120 of FIG. 1.

The cables 3704 are, at least ideally, of equal length, and are flexible. For example, each cable may be formed from strands of a metal such as steel.

While the rodscrew 3700 is unlocked, the cables 3704 are able to slide past one another axially in response to a bending of the rodscrew.

And, while the rodscrew 3700 is in a curved configuration, at least one of the cables 3704 has a slightly different bend radius than at least one other of the cables, and cables with different bend radii each have a slightly different linear length between two arbitrary points along the body of the rodscrew.

While the rodscrew 3700 is locked, positions of the cables 304 relative to one another are fixed such that the cables are unable to slide past one another in an axial dimension.

Therefore, locking the rodscrew 3700 while in a curved configuration causes the rodscrew to be rigid (inflexible) yet to retain a curved shape by fixing the relative positions, and, therefore the bend radii, of the cables 3704.

FIG. 38 is a transparent view of the proximal end 3702 while in an unlocked configuration, according to an embodiment.

The proximal end 3702 is configured to receive cables 3704 within cable slots 3802, and includes a cam 3804 coupled to an engagement receptacle 3806.

While the proximal end 3702 is in an unlocked configuration, the cam 3804 is oriented such that the cables 3704, which may be similar to the cables 118 of FIG. 1, are free to slide within the cable slots 3802, and, therefore, are free to slide relative to one another axially.

FIG. 39 is a transparent view of the proximal end 3702 of FIG. 38 while in a locked configuration, according to an embodiment.

While the proximal end 3702 is in a locked configuration, the cam 3804 is oriented such that the cam compresses the cables 3704 against the inner wall(s) of a housing 3902 of the proximal end 3702 such that the cables are not free to slide axially relative to one another, and, therefore, are in respective fixed positions, at least axially, relative to each other.

Referring to FIGS. 38-39, operation of the proximal end 3702 is described, according to an embodiment.

To transition the proximal end 3702 from an unlocked configuration (FIG. 38) to a locked configuration (FIG. 39), one inserts a tool (e.g., a hexagonal wrench, not shown in FIGS. 38-39) into the receptacle 3806 and rotates the cam 3804 clockwise until the cam engages the cables 3704 and compresses them against the inner wall(s) of the housing 3902.

And to transition the proximal end 3702 from a locked configuration (FIG. 39) to an unlocked configuration (FIG. 38), one inserts a tool (e.g., a hexagonal wrench, not shown in FIGS. 38-39) into the receptacle 3806 and rotates the cam 3804 counterclockwise until the cam disengages and releases the cables 3704 such that the cables are no longer compressed against the inner wall(s) of the housing 3902.

Still referring to FIGS. 37-39, alternate embodiments of the rodscrew proximal end 3702 and the locking and unlocking procedures are contemplated. For example, one or more embodiments described in conjunction with FIGS. 1-36 may be applicable to the proximal end 3702.

EXAMPLE EMBODIMENTS

Example 1 includes a body bead for a bone fracture fixation device, the body bead comprising: at least one pocket each configured to engage a respective one of at least one tab of an adjacent body bead and to withstand, without being significantly deformed, a torque of at least three N·m while rotating with the adjacent body bead; and at least one tab each configured to engage a respective one of at least one pocket of another adjacent body bead and to withstand, without being significantly deformed, a torque of at least three N·m while rotating with the other adjacent body bead.

Example 2 includes the body bead of Example 1, further comprising: a base having first and second ends; wherein each of the at least one pocket is formed in the base at one of the first and second ends; and wherein each of the at least one tab protrudes from another of the first and second ends.

Example 3 includes the body bead of any of Examples 1-2, further comprising: a base having an end; wherein each of the at least one pocket is formed in a respective portion of the base at the end; and wherein each respective portion of the base is configured to withstand, without being significantly deformed, a torque of at least three N·m while rotating with the adjacent body bead.

Example 4 includes the body bead of any of Examples 1-3 wherein each of the at least one pocket includes: a respective pocket neck; and a respective pocket head adjacent to the respective pocket neck.

Example 5 includes the body bead of any of Examples 1-4 wherein each of the at least one pocket includes: a respective pocket neck having a uniform width; and a respective pocket head adjacent to the respective pocket neck and having a circular cross section.

Example 6 includes the body bead of any of Examples 1-5 wherein each of the at least one tab includes: a respective tab neck; and a respective tab head adjacent to the respective tab neck.

Example 7 includes the body bead of any of Examples 1-6 wherein each of the at least tab includes: a respective tab neck having a uniform width; and a respective tab head adjacent to the respective tab neck and having a circular cross section.

Example 8 includes a bone fracture fixation device, comprising: a first interface configured to engage a bone; a second interface configured to engage a bone; a body including a series of beads disposed between, and coupled to, the first interface and the second interface, each bead in the series of beads including three or more cable through holes and each bead configured to withstand, without being significantly deformed, a torque of at least three N·m; three or more cables each disposed in a respective one of the cable through holes; and a locking interface disposed adjacent to one of the first and second interfaces, configurable to hold the cables to cause the body to be rigid in a curved configuration, and configurable to release the cables to cause the body to be flexible.

Example 9 includes the bone-fracture fixation device of Example 8, wherein each of the beads comprises: at least one pocket each configured to engage a respective one of at least one tab of an adjacent bead; and at least one tab each configured to engage a respective one of at least one pocket of another adjacent bead.

Example 10 includes the bone-fracture fixation device of any of Examples 8-9 wherein: each of the at least one pocket includes a respective pocket neck having a pocket width, and a respective pocket head adjacent to the respective pocket neck and having a circular cross section with a pocket diameter; and each of the at least one tab includes a respective tab neck having a tab width that is less than the pocket width; and a respective tab head adjacent to the respective tab neck and having a circular cross section with a tab diameter than is less than the pocket diameter.

Example 11 includes a body bead for a bone fracture fixation device, the body bead comprising: a base having first and second ends and a base width; at least one tab each protruding from the first end, configured to engage a respective one of at least one pocket of an adjacent body bead, and having a respective tab thickness at least approximately one fourth the base width; and at least one pocket each formed in the base at the second end and configured to engage a respective one of at least one tab of another adjacent body bead.

Example 12 includes the body bead of Example 11, wherein: the base has a cylindrical shape; the base width is a base diameter; and each of the at least one tab is positioned along a diameter of the base such that the respective tab thickness is in approximately a same dimension as the diameter.

Example 13 includes the body bead of any of Examples 11-12, wherein: the base has a base height from the second end to the first end; and each of the at least one tab protrudes a tab height that is in an approximate range of one fourth the base height to the base height.

Example 14 includes the body bead of any of Examples 11-13, wherein: the base has a base height of approximately 7.5 mm from the second end to the first end; and each of the at least one tab protrudes a tab height of approximately 4.1 mm.

Example 15 includes the body bead of any of Examples 11-14 wherein each of the at least one tab includes: a respective tab neck; and a respective tab head adjacent to the respective tab neck.

Example 16 includes the body bead of any of Examples 11-15 wherein each of the at least tab includes: a respective tab neck having a width; and a respective tab head adjacent to the respective tab neck and having a circular cross section.

Example 17 includes the body bead of any of Examples 11-16 wherein each of the at least tab includes: a respective tab neck having a tab-neck width; and a respective tab head adjacent to the respective tab neck and having a circular cross section with a diameter that is approximately twice the tab-neck width.

Example 18 includes the body bead of any of Examples 11-17 wherein each of the at least one pocket includes: a respective pocket neck; and a respective pocket head adjacent to the respective pocket neck.

Example 19 includes the body bead of any of Examples 11-18 wherein each of the at least one pocket includes: a respective pocket neck having a width; and a respective pocket head adjacent to the respective pocket neck and having a circular cross section.

Example 20 includes the body bead of any of Examples 11-19, wherein: the base has a cylindrical shape; the base width is a base diameter; and the at least one pocket includes a single pocket that extends through the base along a diameter of the base.

Example 21 includes the body bead of any of Examples 11-20, wherein: the base has a base height from the second end to the first end; and each of the at least pocket has a height from the second end that is in an approximate range of three tenths the base height to nine tenths the base height.

Example 22 includes the body bead of any of Examples 11-21, wherein: the base has a base height from the second end to the first end; and each of the at least pocket has a height from the second end that is in an approximate range of one half the base height to three fifths the base height.

Example 23 includes the body bead of any of Examples 11-22 wherein each of the at least one pocket includes: a respective pocket neck having a pocket-neck width; and a respective pocket head adjacent to the respective pocket neck and having a circular cross section with a diameter that is approximately twice the pocket-neck width.

Example 24 includes the body bead of any of Examples 11-23, further comprising: wherein the base has a cylindrical shape; wherein the base width is a base diameter; a central through hole extending between the first and second ends of the base and having a central-through-hole diameter in an approximate range of one eighth to three eighths of the base diameter; and wherein the at least one tab includes two tabs positioned on opposite sides of the central through hole, each of the two tabs positioned along a diameter of the base such that the respective tab thickness is in approximately a same dimension as the diameter.

Example 25 includes the body bead of any of Examples 11-24, further comprising: wherein the base has a cylindrical shape; wherein the base width is a base diameter; a central through hole extending between the first and second ends of the base and having a central-through-hole diameter in an approximate range of one eighth to three eighths of the base diameter; a chamfer formed in the first end of the base around the central through hole and having a chamfer thickness; and wherein the at least one tab includes two tabs positioned on opposite sides of the central through hole, each of the two tabs positioned along a diameter of the base such that the respective tab thickness is in approximately a same dimension as the diameter, and each of the two tabs has approximately the same thickness such that the sum of the central-through-hole diameter, the chamber thickness, and the thicknesses of the two tabs is approximately equal to the base diameter.

Example 26 includes the body bead of any of Examples 11-25, further comprising: wherein the base has a cylindrical shape; wherein the base width is a base diameter; a central through hole extending between the first and second ends of the base; and wherein the at least one tab includes two tabs positioned on opposite sides of the central through hole, each of the two tabs positioned along a diameter of the base such that the respective tab thickness is in approximately a same dimension as the diameter, each tab having a respective chamfered surface that faces the central through hole and that tapers away from the central through hole in a direction away from the base.

Example 27 includes the body bead of any of Examples 11-26, further comprising: wherein the base has a cylindrical shape; wherein the base width is a base diameter; and cable through holes extending between the first and second ends of the base, approximately evenly spaced in a circumferential dimension, and each having a cable-through-hole diameter in an approximate range of three one hundredths to three tenths of the base diameter.

Example 28 includes the body bead of any of Examples 11-27, further comprising: wherein the base has a cylindrical shape; wherein the base width is a base diameter; four cable through holes extending between the first and second ends of the base, approximately evenly spaced in a circumferential dimension, and each having a cable-through-hole diameter of approximately three twentieths the base diameter; and wherein the at least one tab includes two tabs each positioned along a diameter of the base such that the respective tab thickness is in approximately a same dimension as the diameter, each tab disposed between a respective two of the cable through holes and having curved sides that each approximately follow a curvature of a respective adjacent one of the cable through holes.

Example 29 includes the body bead of any of Examples 11-28, further comprising: wherein the base has a cylindrical shape; wherein the base width is a base diameter; four cable through holes extending between the first and second ends of the base, approximately evenly spaced in a circle having a diameter in an approximate range of one half to three quarters the base diameter, and each having a cable-through-hole diameter of approximately three twentieths the base diameter; and wherein the at least one tab includes two tabs each positioned along a diameter of the base such that the respective tab thickness is in approximately a same dimension as the diameter, each tab disposed between a respective two of the cable through holes and having curved sides that each approximately follow a curvature of a respective adjacent one of the cable through holes.

Example 30. The body bead of any of Examples 11-29, further comprising: wherein the base has a cylindrical shape; wherein the base width is a base diameter; four cable through holes extending between the first and second ends of the base, approximately evenly spaced in a circumferential dimension, each having a cable-through-hole diameter of approximately three twentieths the base diameter, and each having chamfered edges at the first and second ends of the base; and wherein the at least one tab includes two tabs each positioned along a diameter of the base such that the respective tab thickness is in approximately a same dimension as the diameter, each tab disposed between a respective two of the cable through holes and having curved sides that each approximately follow a curvature of a respective adjacent one of the cable through holes.

Example 31 includes a bone-fracture fixation device, comprising: a distal interface configured to engage a bone; a proximal interface a body including a series of beads disposed between, and coupled to, the distal and proximal interfaces, each bead in the series of beads including a base having first and second ends and a base width, at least one tab each protruding from the first end, configured to engage a respective one of at least one pocket of an adjacent body bead, and having a respective tab thickness at least approximately one fourth the base width; and at least one pocket each formed in the base at the second end and configured to engage a respective one of at least one tab of another adjacent body bead; and a locking interface disposed adjacent to the proximal interface, configurable to cause the body to be rigid in a curved configuration, and configurable to cause the body to be flexible.

Example 32 includes the bone-fracture fixation device of Example 31, wherein: the base has a cylindrical shape; the base width is a base diameter; and each of the at least one tab is positioned along a diameter of the base such that the respective tab thickness is in approximately a same dimension as the diameter.

Example 33 includes the bone-fracture fixation device of any of Examples 31-32, wherein: the base has a base height from the second end to the first end; and each of the at least one tab protrudes a tab height that is in an approximate range of one fourth the base height to the base height.

Example 34 includes the bone-fracture fixation device of any of Examples 31-33, wherein: the base has a base height of approximately 7.5 mm from the second end to the first end; and each of the at least one tab protrudes a tab height of approximately 4.1 mm.

Example 35 includes the bone-fracture fixation device of any of Examples 31-34 wherein each of the at least one tab includes: a respective tab neck; and a respective tab head adjacent to the respective tab neck.

Example 36 includes the bone-fracture fixation device of any of Examples 31-35 wherein each of the at least tab includes: a respective tab neck having a width; and a respective tab head adjacent to the respective tab neck and having a circular cross section.

Example 37 includes the bone-fracture fixation device of any of Examples 31-36 wherein each of the at least tab includes: a respective tab neck having a tab-neck width; and a respective tab head adjacent to the respective tab neck and having a circular cross section with a diameter that is approximately twice the tab-neck width.

Example 38 includes the bone-fracture fixation device of any of Examples 31-37 wherein each of the at least one pocket includes: a respective pocket neck; and a respective pocket head adjacent to the respective pocket neck.

Example 39 includes the bone-fracture fixation device of any of Examples 31-38 wherein each of the at least one pocket includes: a respective pocket neck having a width; and a respective pocket head adjacent to the respective pocket neck and having a circular cross section.

Example 40 includes the bone-fracture fixation device of any of Examples 31-39 wherein: the base has a cylindrical shape; the base width is a base diameter; and the at least one pocket includes a single pocket that extends through the base along a diameter of the base.

Example 41 includes the bone-fracture fixation device of any of Examples 31-40 wherein: the base has a base height from the second end to the first end; and each of the at least pocket has a height from the second end that is in an approximate range of three tenths the base height to nine tenths the base height.

Example 42 includes the bone-fracture fixation device of any of Examples 31-41 wherein: the base has a base height from the second end to the first end; and each of the at least pocket has a height from the second end that is in an approximate range of one half the base height to three fifths the base height.

Example 43 includes the bone-fracture fixation device of any of Examples 31-42 wherein each of the at least one pocket includes: a respective pocket neck having a pocket-neck width; and a respective pocket head adjacent to the respective pocket neck and having a circular cross section with a diameter that is approximately twice the pocket-neck width.

Example 44 includes the bone-fracture fixation device of any of Examples 31-43, further comprising: wherein the base has a cylindrical shape; wherein the base width is a base diameter; a central through hole extending between the first and second ends of the base and having a central-through-hole diameter in an approximate range of one eighth to three eighths of the base diameter; and wherein the at least one tab includes two tabs positioned on opposite sides of the central through hole, each of the two tabs positioned along a diameter of the base such that the respective tab thickness is in approximately a same dimension as the diameter.

Example 45 includes the bone-fracture fixation device of any of Examples 31-44, further comprising: wherein the base has a cylindrical shape; wherein the base width is a base diameter; a central through hole extending between the first and second ends of the base and having a central-through-hole diameter in an approximate range of one eighth to three eighths of the base diameter; a chamfer formed in the first end of the base around the central through hole and having a chamfer thickness; and wherein the at least one tab includes two tabs positioned on opposite sides of the central through hole, each of the two tabs positioned along a diameter of the base such that the respective tab thickness is in approximately a same dimension as the diameter, and each of the two tabs has approximately the same thickness such that the sum of the central-through-hole diameter, the chamber thickness, and the thicknesses of the two tabs is approximately equal to the base diameter.

Example 46 includes the bone-fracture fixation device of any of Examples 31-45, further comprising: wherein the base has a cylindrical shape; wherein the base width is a base diameter; a central through hole extending between the first and second ends of the base; and wherein the at least one tab includes two tabs positioned on opposite sides of the central through hole, each of the two tabs positioned along a diameter of the base such that the respective tab thickness is in approximately a same dimension as the diameter, each tab having a respective chamfered surface that faces the central through hole and that tapers away from the central through hole in a direction away from the base.

Example 47 includes the bone-fracture fixation device of any of Examples 31-46, further comprising: wherein the base has a cylindrical shape; wherein the base width is a base diameter; and cable through holes extending between the first and second ends of the base, approximately evenly spaced in a circumferential dimension, and each having a cable-through-hole diameter in an approximate range of three one hundredths to three tenths of the base diameter.

Example 48 includes the bone-fracture fixation device of any of Examples 31-47, further comprising: wherein the base has a cylindrical shape; wherein the base width is a base diameter; four cable through holes extending between the first and second ends of the base, approximately evenly spaced in a circumferential dimension, and each having a cable-through-hole diameter of approximately three twentieths the base diameter; and wherein the at least one tab includes two tabs each positioned along a diameter of the base such that the respective tab thickness is in approximately a same dimension as the diameter, each tab disposed between a respective two of the cable through holes and having curved sides that each approximately follow a curvature of a respective adjacent one of the cable through holes.

Example 49 includes the bone-fracture fixation device of any of Examples 31-48, further comprising: wherein the base has a cylindrical shape; wherein the base width is a base diameter; four cable through holes extending between the first and second ends of the base, approximately evenly spaced in a circle having a diameter in an approximate range of one half to three quarters the base diameter, and each having a cable-through-hole diameter of approximately three twentieths the base diameter; and wherein the at least one tab includes two tabs each positioned along a diameter of the base such that the respective tab thickness is in approximately a same dimension as the diameter, each tab disposed between a respective two of the cable through holes and having curved sides that each approximately follow a curvature of a respective adjacent one of the cable through holes.

Example 50 includes the bone-fracture fixation device of any of Examples 31-49, further comprising: wherein the base has a cylindrical shape; wherein the base width is a base diameter; four cable through holes extending between the first and second ends of the base, approximately evenly spaced in a circumferential dimension, each having a cable-through-hole diameter of approximately three twentieths the base diameter, and each having chamfered edges at the first and second ends of the base; and wherein the at least one tab includes two tabs each positioned along a diameter of the base such that the respective tab thickness is in approximately a same dimension as the diameter, each tab disposed between a respective two of the cable through holes and having curved sides that each approximately follow a curvature of a respective adjacent one of the cable through holes.

Example 51 includes the bone-fracture fixation device of any of Examples 31-50, further comprising: wherein the base has a cylindrical shape; wherein the base width is a base diameter; three or more cable through holes extending between the first and second ends of the base, approximately evenly spaced in a circumferential dimension, and each having a cable-through-hole diameter in an approximate range of three one hundredths to three tenths of the base diameter; three or more cables each disposed in respective ones of the cable through holes of the body beads; and wherein the locking interface is configurable to hold the cables to cause the body to be rigid in a curved configuration, and is configurable to release the fibers to cause the body to be flexible.

Example 52 includes the bone-fracture fixation device of any of Examples 31-51, further comprising: wherein the base has a cylindrical shape; wherein the base width is a base diameter; four cable through holes extending between the first and second ends of the base, approximately evenly spaced in a circumferential dimension, and each having a cable-through-hole diameter of approximately three twentieths the base diameter; wherein the at least one tab includes two tabs each positioned along a diameter of the base such that the respective tab thickness is in approximately a same dimension as the diameter, each tab disposed between a respective two of the cable through holes and having curved sides that each approximately follow a curvature of a respective adjacent one of the cable through holes; and four cables each disposed in respective ones of the cable through holes of the body beads; and wherein the locking interface is configurable to hold the cables to cause the body to be rigid in a curved configuration, and is configurable to release the fibers to cause the body to be flexible.

Example 53 includes the bone-fracture fixation device of any of Examples 31-52, further comprising: wherein the base has a cylindrical shape; wherein the base width is a base diameter; four cable through holes extending between the first and second ends of the base, approximately evenly spaced in a circle having a diameter in an approximate range of one half to three quarters the base diameter, and each having a cable-through-hole diameter of approximately three twentieths the base diameter; wherein the at least one tab includes two tabs each positioned along a diameter of the base such that the respective tab thickness is in approximately a same dimension as the diameter, each tab disposed between a respective two of the cable through holes and having curved sides that each approximately follow a curvature of a respective adjacent one of the cable through holes; four cables each disposed in respective ones of the cable through holes of the body beads; and wherein the locking interface is configurable to hold the cables to cause the body to be rigid in a curved configuration, and is configurable to release the fibers to cause the body to be flexible.

Example 54 includes the bone-fracture fixation device of any of Examples 31-53, further comprising: wherein the base has a cylindrical shape; wherein the base width is a base diameter; four cable through holes extending between the first and second ends of the base, approximately evenly spaced in a circumferential dimension, each having a cablethrough-hole diameter of approximately three twentieths the base diameter, and each having chamfered edges at the first and second ends of the base; wherein the at least one tab includes two tabs each positioned along a diameter of the base such that the respective tab thickness is in approximately a same dimension as the diameter, each tab disposed between a respective two of the cable through holes and having curved sides that each approximately follow a curvature of a respective adjacent one of the cable through holes; four cables each disposed in respective ones of the cable through holes of the body beads; and wherein the locking interface is configurable to hold the cables to cause the body to be rigid in a curved configuration, and is configurable to release the fibers to cause the body to be flexible.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated. Moreover, one or more components of a described apparatus or system, or one or more steps of a described method, may have been omitted from the description for clarity or for another reason. In addition, one or more components of a described apparatus or system that have been included in the description may be omitted from the apparatus or system, and one or more steps of a described method that have been included in the description may be omitted from the method.

The invention claimed is:

1. A body bead for a bone fracture fixation device, the body bead comprising:
    a base having a cylindrical shape and extending longitudinally between first and second ends, the base having a base diameter;
    at least one tab each protruding from the first end in a direction away from the base, configured to engage a respective one of at least one pocket of an adjacent body bead, and having a respective tab thickness at least one fourth the base width, wherein each of the at least one tab is positioned along a diameter of the base such that the respective tab thickness is in approximately a same dimension as the diameter; and
    at least one pocket each formed in the base at the second end and configured to engage a respective one of at least one tab of another adjacent body bead.

2. The body bead of claim 1, wherein:
    the base has a base height from the second end to the first end; and
    each of the at least one tab protrudes a tab height that is in an approximate range of one fourth the base height to the base height.

3. The body bead of claim 1, wherein:
    the base has a base height of approximately 7.5 mm from the second end to the first end; and
    each of the at least one tab protrudes a tab height of approximately 4.1 mm.

4. The body bead of claim 1 wherein each of the at least one tab includes:
    a respective tab neck; and
    a respective tab head adjacent to the respective tab neck.

5. The body bead of claim 1 wherein each of the at least one tab includes:
    a respective tab neck having a width; and
    a respective tab head adjacent to the respective tab neck and having a circular cross section.

6. The body bead of claim 1 wherein each of the at least one tab includes:

a respective tab neck having a tab-neck width; and a respective tab head adjacent to the respective tab neck and having a circular cross section with a diameter that is approximately twice the tab-neck width.

7. The body bead of claim 1 wherein each of the at least one pocket includes:

a respective pocket neck; and a respective pocket head adjacent to the respective pocket neck.

8. The body bead of claim 1 wherein each of the at least one pocket includes:

a respective pocket neck having a width; and a respective pocket head adjacent to the respective pocket neck and having a circular cross section.

9. The body bead of claim 1, wherein:

the base has a cylindrical shape; and the at least one pocket includes a single pocket that extends through the base along a diameter of the base.

10. The body bead of claim 1, wherein:

the base has a base height from the second end to the first end; and each of the at least pocket has a height from the second end that is in an approximate range of three tenths the base height to nine tenths the base height.

11. The body bead of claim 1, wherein:

the base has a base height from the second end to the first end; and each of the at least pocket has a height from the second end that is in an approximate range of one half the base height to three fifths the base height.

12. The body bead of claim 1 wherein each of the at least one pocket includes:

a respective pocket neck having a pocket-neck width; and a respective pocket head adjacent to the respective pocket neck and having a circular cross section with a diameter that is approximately twice the pocket-neck width.

13. The body bead of claim 1, further comprising:

wherein the base has a cylindrical shape;

a central through-hole extending between the first and second ends of the base and having a central through-hole diameter in an approximate range of one eighth to three eighths of the base diameter; and wherein the at least one tab includes two tabs positioned on opposite sides of the central through-hole, each of the two tabs positioned along a diameter of the base such that the respective tab thickness is in approximately a same dimension as the diameter.

14. The body bead of claim 1, further comprising:

wherein the base has a cylindrical shape;

a central through-hole extending between the first and second ends of the base and having a central-through-hole diameter in an approximate range of one eighth to three eighths of the base diameter;

a chamfer formed in the first end of the base around the central through-hole and having a chamfer thickness; and wherein the at least one tab includes two tabs positioned on opposite sides of the central through-hole, each of the two tabs positioned along a diameter of the base such that the respective tab thickness is in approximately a same dimension as the diameter, and each of the two tabs has approximately the same thickness such that the sum of the central-through-hole diameter, the chamber thickness, and the thicknesses of the two tabs is approximately equal to the base diameter.

15. The body bead of claim 1, further comprising:

wherein the base has a cylindrical shape;

a central through-hole extending between the first and second ends of the base; and wherein the at least one tab includes two tabs positioned on opposite sides of the central through-hole, each of the two tabs positioned along a diameter of the base such that the respective tab thickness is in approximately a same dimension as the diameter, each tab having a respective chamfered surface that faces the central through-hole and that tapers away from the central through-hole in a direction away from the base.

16. The body bead of claim 1, further comprising:

wherein the base has a cylindrical shape;

cable through-holes extending between the first and second ends of the base, approximately evenly spaced in a circumferential dimension, and each having a cable through-hole diameter in an approximate range of three one hundredths to three tenths of the base diameter.

17. The body bead of claim 1, further comprising:

wherein the base has a cylindrical shape;

four cable through-holes extending between the first and second ends of the base, approximately evenly spaced in a circumferential dimension, and each having a cable-through-hole diameter of approximately three twentieths the base diameter; and wherein the at least one tab includes two tabs each positioned along a diameter of the base such that the respective tab thickness is in approximately a same dimension as the diameter, each tab disposed between a respective two of the cable through-holes and having curved sides that each approximately follow a curvature of a respective adjacent one of the cable through-holes.

18. The body bead of claim 1, further comprising:

wherein the base has a cylindrical shape;

four cable through-holes extending between the first and second ends of the base, approximately evenly spaced in a circle having a diameter in an approximate range of one half to three quarters the base diameter, and each having a cable-through-hole diameter of approximately three twentieths the base diameter; and wherein the at least one tab includes two tabs each positioned along a diameter of the base such that the respective tab thickness is in approximately a same dimension as the diameter, each tab disposed between a respective two of the cable through-holes and having curved sides that each approximately follow a curvature of a respective adjacent one of the cable through-holes.

19. The body bead of claim 1, further comprising:

wherein the base has a cylindrical shape;

four cable through-holes extending between the first and second ends of the base, approximately evenly spaced in a circumferential dimension, each having a cable-through-hole diameter of approximately three twentieths the base diameter, and each having chamfered edges at the first and second ends of the base; and wherein the at least one tab includes two tabs each positioned along a diameter of the base such that the respective tab thickness is in approximately a same dimension as the diameter, each tab disposed between a respective two of the cable through-holes and having curved sides that each approximately follow a curvature of a respective adjacent one of the cable through-holes.

20. A body bead for a bone fracture fixation device, the body bead comprising:

a base having a cylindrical shape, first and second ends, and a base diameter;

at least one tab each protruding from the first end, configured to be received within a respective one of at least one pocket of an adjacent body bead, and having a respective tab thickness at least one fourth the base width, wherein each of the at least one tab is positioned along a diameter of the base such that the respective tab thickness is in approximately a same dimension as the diameter; and at least one pocket each formed in the base at the second end and configured to receive a respective one of at least one tab of another adjacent body bead.

21. The body bead of claim 20, wherein:

the base has a base height from the second end to the first end; and each of the at least one tab protrudes a tab height that is in an approximate range of one fourth the base height to the base height.

22. The body bead of claim 20, wherein:

the base has a base height of approximately 7.5 mm from the second end to the first end; and each of the at least one tab protrudes a tab height of approximately 4.1 mm.

23. The body bead of claim 20, wherein each of the at least one tab includes:

a respective tab neck; and a respective tab head adjacent to the respective tab neck.

24. The body bead of claim 20, wherein each of the at least tab includes:

a respective tab neck having a width; and a respective tab head adjacent to the respective tab neck and having a circular cross section.

25. The body bead of claim 20, wherein each of the at least tab includes:

a respective tab neck having a tab-neck width; and a respective tab head adjacent to the respective tab neck and having a circular cross section with a diameter that is approximately twice the tab-neck width.

26. The body bead of claim 20, wherein each of the at least one pocket includes:

a respective pocket neck; and a respective pocket head adjacent to the respective pocket neck.

27. The body bead of claim 20, wherein each of the at least one pocket includes:

a respective pocket neck having a width; and a respective pocket head adjacent to the respective pocket neck and having a circular cross section.

28. The body bead of claim 20, wherein:

the base has a cylindrical shape;

the at least one pocket includes a single pocket that extends through the base along a diameter of the base.

29. The body bead of claim 20, wherein:

the base has a base height from the second end to the first end; and each of the at least pocket has a height from the second end that is in an approximate range of three tenths the base height to nine tenths the base height.

30. The body bead of claim 20, wherein:

the base has a base height from the second end to the first end; and each of the at least pocket has a height from the second end that is in an approximate range of one half the base height to three fifths the base height.

31. The body bead of claim 20, wherein each of the at least one pocket includes:

a respective pocket neck having a pocket-neck width; and a respective pocket head adjacent to the respective pocket neck and having a circular cross section with a diameter that is approximately twice the pocket-neck width.

32. A body bead for a bone fracture fixation device, the body bead comprising:

a base extending longitudinally between first and second ends, a base width, and a base height from the second end to the first end;

at least one tab each protruding from the first end in a direction away from the base, configured to engage a respective one of at least one pocket of an adjacent body bead, and having a respective tab thickness at least one fourth the base width, wherein each of the at least one tab protrudes a tab height that is in an approximate range of one fourth the base height to the base height; and at least one pocket each formed in the base at the second end and configured to engage a respective one of at least one tab of another adjacent body bead.

33. A body bead for a bone fracture fixation device, the body bead comprising:

a base having first and second ends, a base width, and a base height from the second end to the first end;

at least one tab each protruding from the first end, configured to be received within a respective one of at least one pocket of an adjacent body bead, and having a respective tab thickness at least one fourth the base width, each of the at least one tab protrudes a tab height that is in an approximate range of one fourth the base height to the base height; and at least one pocket each formed in the base at the second end and configured to receive a respective one of at least one tab of another adjacent body bead.

* * * * *